United States Patent
Baker et al.

(10) Patent No.: US 9,302,025 B2
(45) Date of Patent: *Apr. 5, 2016

(54) HEMOSTATIC COMPOSITIONS AND METHODS OF USE

(71) Applicant: The Regents of the University of California, Oakland, CA (US)

(72) Inventors: Sarah Baker, Santa Barbara, CA (US); April Sawvel, Santa Barbara, CA (US); Galen D. Stucky, Santa Barbara, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/198,395

(22) Filed: Mar. 5, 2014

(65) Prior Publication Data

US 2014/0308337 A1   Oct. 16, 2014

Related U.S. Application Data

(63) Continuation of application No. 12/030,779, filed on Feb. 13, 2008, now Pat. No. 8,703,634.

(60) Provisional application No. 60/902,738, filed on Feb. 21, 2007.

(51) Int. Cl.
  *A61L 15/42* (2006.01)
  *A61L 15/18* (2006.01)
  *A61L 15/32* (2006.01)
  *A61L 15/44* (2006.01)

(52) U.S. Cl.
  CPC ............... *A61L 15/18* (2013.01); *A61L 15/32* (2013.01); *A61L 15/425* (2013.01); *A61L 15/44* (2013.01); *A61L 2400/04* (2013.01)

(58) Field of Classification Search
  CPC .... A61L 15/425; A61L 15/44; A61L 2400/04
  See application file for complete search history.

(56) References Cited

U.S. PATENT DOCUMENTS

| | | | |
|---|---|---|---|
| 3,763,900 A | 10/1973 | Solms-Baruth et al. | |
| 4,373,519 A | 2/1983 | Errede et al. | |
| 4,717,735 A | 1/1988 | Strem | |
| 4,728,323 A | 3/1988 | Matson | |
| 4,748,978 A | 6/1988 | Kamp | |
| 4,822,349 A | 4/1989 | Hursey et al. | |
| 4,828,832 A | 5/1989 | De Cuellar et al. | |
| 6,251,423 B1 | 6/2001 | Bradford | |
| 8,703,634 B2 * | 4/2014 | Baker et al. | 501/141 |
| 2002/0197302 A1 * | 12/2002 | Cochrum et al. | 424/445 |
| 2003/0133990 A1 | 7/2003 | Hursey et al. | |
| 2004/0049144 A1 * | 3/2004 | Cea | 602/41 |
| 2005/0058721 A1 * | 3/2005 | Hursey | 424/618 |
| 2005/0074505 A1 | 4/2005 | Hursey | |
| 2006/0007862 A1 | 1/2006 | Sayeedi et al. | |
| 2006/0034935 A1 | 2/2006 | Pronovost et al. | |
| 2006/0141060 A1 | 6/2006 | Hursey et al. | |
| 2006/0155235 A1 | 7/2006 | Sawyer | |
| 2006/0178609 A1 | 8/2006 | Horn et al. | |
| 2006/0211965 A1 | 9/2006 | Horn et al. | |
| 2006/0211971 A1 | 9/2006 | Horn et al. | |
| 2007/0004995 A1 | 1/2007 | Horn et al. | |
| 2007/0154510 A1 | 7/2007 | Wilcher et al. | |
| 2007/0275073 A1 | 11/2007 | Huey et al. | |
| 2008/0097271 A1 | 4/2008 | Lo et al. | |
| 2008/0125686 A1 | 5/2008 | Lo | |
| 2008/0145455 A1 | 6/2008 | Bedard | |

FOREIGN PATENT DOCUMENTS

| | | |
|---|---|---|
| WO | 2005027808 | 3/2005 |
| WO | 2006088912 | 8/2006 |

OTHER PUBLICATIONS

Carrado et al. "Effects of Surface Functionalization and Organo-Tailoring of Synthetic Layer Silicates on the Immobilization of Cytochrome c." Chemistry of Materials 16:2559-2566 (2004).
Ha, et al. "Facile Assembly of Zeolite Monolayers on Glass, Silica, Alumina, and Other Zeolites Using 3-Halopropylsilyl Reagents as Covalent Linkers," Advanced Materials 12(15):1114-1117 (2000).
Jerez, et al. "Coating of silica sand with aluminosilicate clay," Journal of Colloid and Interface Science 294 (1):155-164 (2006).
Lin et al. "Preparation of Protein-Silicate Hybrids from Polyamine Intercalation of Layered Montmorillonite," Langmuir 23:1995-1999 (2007).
Liu, H., et al. "Synthesis and characterization of kaolin/NaY/MCM-41 composites," Microporous and Mesoporous Materials 66:117-125 (2003).
Mineral Herbal Medicine, edited by Lanzhong Guo 59-61 (1995).
Yoon "Organization of zeolite microcrystals for production of functional materials," Accounts of Chemical Research 40:29-40 (2007).

* cited by examiner

*Primary Examiner* — Ali Soroush
(74) *Attorney, Agent, or Firm* — Rudy J. Ng; Carol L. Francis; Bozicevic, Field & Francis LLP

(57) ABSTRACT

Hemostatic compositions comprising a wet layered clay (e.g., wet kaolin) and, optionally, a zeolite, as well as devices and methods of use to promote blood clotting, are provided.

16 Claims, 8 Drawing Sheets

HEMOSTATIC COMPOSITIONS AND METHODS OF USE

CROSS-REFERENCE TO RELATED APPLICATIONS

This application is a continuation of U.S. application Ser. No. 12/030,779, filed on Feb. 13, 2008, which claims priority benefit of U.S. application Ser. No. 60/902,738, filed Feb. 21, 2007, the disclosures of which applications are incorporated herein in their entirety.

STATEMENT REGARDING FEDERALLY SPONSORED RESEARCH

This invention was made with government support under Grant Number N00014-06-1-0145, awarded by the Office of Naval Research. The government has certain rights in the invention.

BACKGROUND

Treatment of bleeding wounds, particularly severely bleeding wounds, can require immediate attention to bring the bleeding under control. Severe bleeding poses a very real risk of death to the casualty if not treated quickly. Although loss of about 10-15% of total blood volume can be endured without clinical sequelae in a healthy person, if a laceration or penetrating trauma (e.g., knife or gun wound) is severe enough or involves critical arteries or veins, this volume of blood can be lost in a matter of minutes. The bleeding must be slowed immediately or irreversible damage to organs and mortality can result.

Bleeding wounds, even those that may be less severe, can pose serious difficulties and risks when a severe wound is inflicted in a remote area or other≥situations (such as found in a battlefield) where full medical assistance may be not immediately available. In such circumstances it can be critical to undertake measures to slow or stop bleeding so that the subject can be transported to a medical facility.

Various methods and hemostatic compositions for promoting blood clotting have been developed, and can be applied to help control bleeding in such situations. Exemplary compositions include those composed of bound zeolite (see, e.g., U.S. Pat. No. 4,822,349). Such zeolite/binder compositions, such as QuikClot®, can have a water content of about 1.54% or less as estimated by measuring the mass of material before and after heating at 550° C. (i.e., Loss on Ignition (LOI) at 550° C.). Higher temperatures are sometimes used for LOI calculations, but procedures that utilize these higher temperatures increase the loss of chemical compounds other than water. Further exemplary hemostatic compositions include those that composed of partially hydrated zeolite, such as described in US 2005/0059721.

The field continues to develop additional hemostatic compositions that provide for, for example, rapid initiation of blood clotting, increased rate of blood clotting, sufficient blood clot strength, and/or reduced adverse side effects (e.g., due to heat that can be generated locally as a result of enthalpy of hydration that may be associated with use of certain hemostatic agents, such as dry bound zeolite), and which can optionally deliver antibiotics and/or wound healing-promoting agents, and/or pro-thrombotic agents, and/or ions. Of particular interest are such hemostatic compositions that can be rapidly and safely applied in an emergency situation, such as on the battlefield or at the scene of an accident, without the need for intensive training or equipment.

LITERATURE

U.S. Pat. Nos. 4,748,978; 4,822,349; U.S. Pat. No. 4,373,519; US 2003/0133990; US 2005/0074505; US 2005/0058721; US 2006/0141060; US 2007/0004995; US 2006/0211971; US 2006/0211965; US 2006/007862; US 2006/0155235; WO 06/088912.

Jerez et al. "Coating of silica sand with aluminosilicate clay." Journal of Colloid and Interface Science 2006, 294(1): 155-164; Liu et al. Microporous and Mesoporous Materials 2003, 66:117; Ha et al. Advanced Materials 2000, 12, 1114; and Yoon Accounts of Chemical Research 2007, 40:29; Lin et al. (2007) "Preparation of Protein-Silicate Hybrids from Polyamine Intercalation of Layered Montmorillonite." Langmuir 23:1995-1999; Carrado et al. (2004) "Effects of Surface Functionalization and Organo-Tailoring of Synthetic Layer Silicates on the Immobilization of Cytochrome c." Chemistry of Materials 16:2559-2566.

SUMMARY

Hemostatic compositions comprising a wet layered clay (e.g., wet kaolin) and, optionally, a zeolite, as well as devices and methods of use to promote blood clotting, are provided.

In one embodiment, the disclosure provides a device containing a hemostatic composition comprising a sterile container; and a hemostatically effective amount of a wet layered clay selected from a kaolin, a smectite, palygorskite or sepiolite, wherein the layered clay is provided in the sterile container. In related embodiments, the wet layered clay is kaolin or a smectite, e.g., a wet montmorillonite. In further related embodiments, the wet layered clay is combined with a clotting factor polypeptide or a thrombin polypeptide. In related embodiments, the hemostatic composition comprises a substrate adapted for delivery of the wet layered clay to a bleeding wound, e.g., a bandage or a medical sponge. In another embodiment, the hemostatic composition further comprises zeolite, which may be at least partially dehydrated.

In another embodiment the disclosure provides a hemostatic composition comprises a) an isolated wet layered clay selected from a kaolin, a smectite, palygorskite or sepiolite; and b) an isolated zeolite, wherein the wet layered clay and the zeolite are present to provide for hemostatic activity of the composition. In related embodiments, the wet layered clay is kaolin or a smectite, e.g., a wet montmorillonite. In some embodiments, the zeolite is at least partially dehydrated. In further embodiments, the at least partially dehydrated zeolite has a moisture content of from 1 wt. % to 10 wt. % water. In other further embodiments, in further embodiments, the at least partially dehydrated zeolite has a moisture content of 1 wt. % to 4 wt. % water. In further embodiments, the zeolite is disposed in a binder. In other embodiments, the wet layered clay and the zeolite are present in the hemostatic composition at a ratio of greater than 1:1 by weight. In related embodiments, the hemostatic composition is disposed on at least one surface of a device adapted for delivery of the isolated layered clay to a bleeding wound. In related embodiments, the device is a bandage or a medical sponge.

In further embodiments, the disclosure provides a method of forming a hemostatic composition, the method comprising combining a zeolite with a wet layered clay selected from selected from a kaolin, a smectite, palygorskite or sepiolite wherein said combining forms a hemostatic composition. In related embodiments, the zeolite is at least partially dehydrated prior to said combining.

In other embodiments, the disclosure provides a method of clotting blood flowing from a wound, comprising applying a hemostatic composition disclosed herein to a bleeding wound of a subject; and maintaining the hemostatic composition in contact with the wound for a period of time sufficient to at least initiate blood clotting.

These and other embodiments of the invention will be readily apparent to the ordinarily skilled artisan upon reading the present specification.

DEFINITIONS

Figure 1:
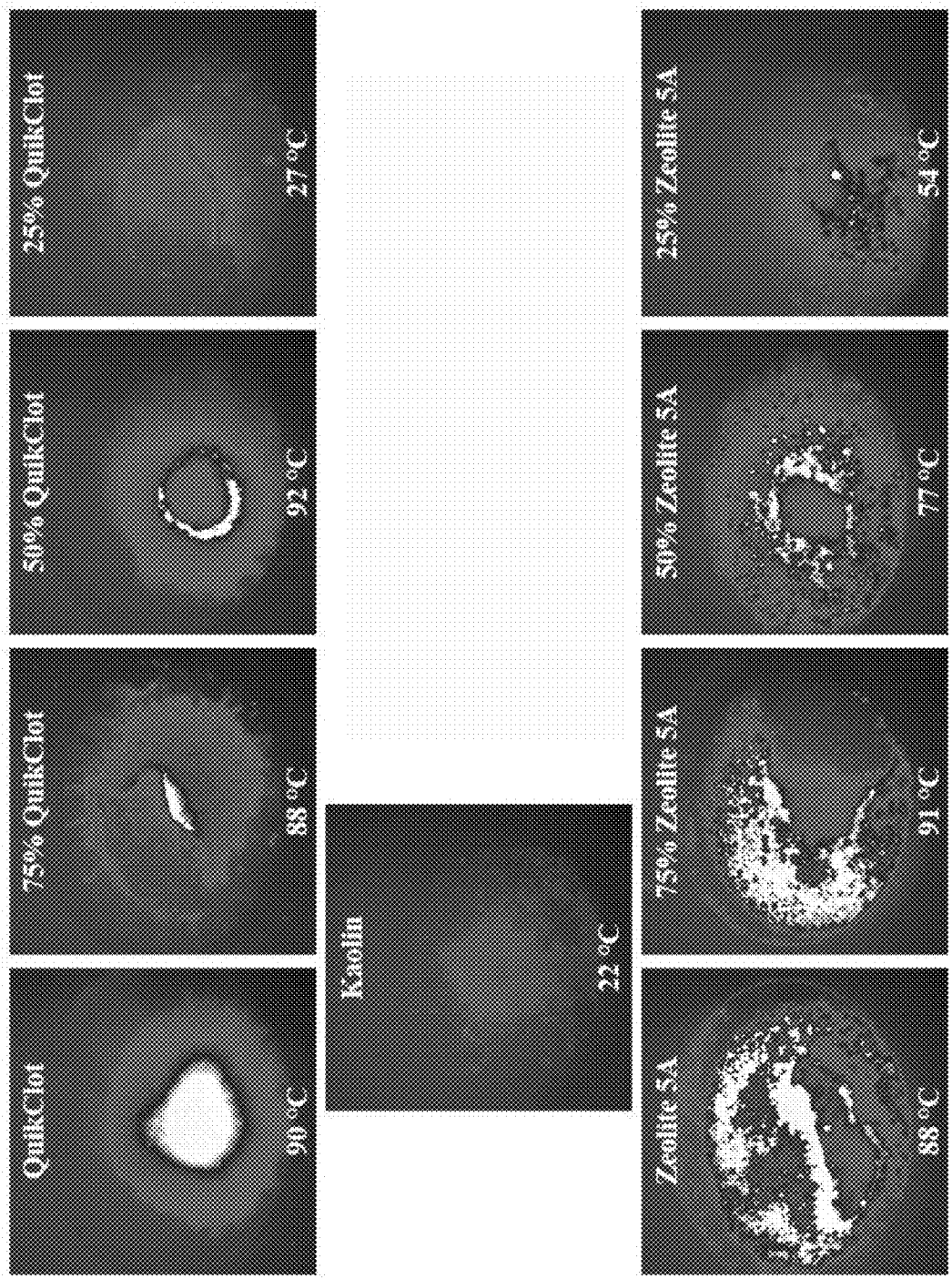
FIG. 1 is a collection of thermal images of heat release by QUIKCLOT®, zeolite 5A, and mixtures of wet kaolin with dry QUIKCLOT® or dry zeolite 5A. Each sample is a physical mixture with Kaolin (wt % reported). Both the QuickClot® and Zeolite 5A were fully dehydrated. Temperature readings were taken at the hottest part of the sample. The hottest portions of the sample appear in the figure in white, with the temperature indicating the hottest areas of the sample.

A "hemostatic agent" refers to an agent which promotes blood clotting, e.g., following administration to a wound.

A "hemostatic composition" refers to a composition comprising at least one hemostatic agent, and further includes at least one or more additional components, which may be hemostatically active (e.g., promote blood clotting or promote activity of the hemostatic agent in the hemostatic composition in blood clotting) or hemostatically inert.

The term "hemostasis" as used herein refers to inhibition of bleeding, including the arrest of bleeding, which is accompanied by blood clot formation.

A "hemostatically effective amount" refers to an amount of a hemostatic composition which, following application to a bleeding wound, is effective to facilitate blood clotting (e.g., as compared to time to clot formation in the absence of the hemostatic agent), increase blood clotting rate as compared to a blood clotting rate in the absences of the hemostatic agent, and/or improve blood clot strength as compared to blood clot strength in the absence of the hemostatic agent. Clot strength can be measured by Thrombelastograph® measurements. Assays for assessing hemostatic activity are known in the art, with exemplary methods described herein.

"Hydration" generally refers to a level or amount of water associated with a compound, and is meant to encompass physisorbed water and chemisorbed water. Physisorbed water refers to water molecules that are associated with a surface of a compound through Van der Waals forces. Chemisorbed water refers to water molecules that adhere to a surface of a compound through the formation of a chemical bond, e.g., hydrogen bond or a coordinate bond, e.g., between an oxygen atom of a water molecule and a metal atom.

"Dehydration" refers to removal of water molecules from a compound, which involves removal of all or a portion of physisorbed water, and/or all or a portion of chemisorbed water. It is well understood that upon application of heat, physisorbed water is more readily removed than chemisorbed water. In general, application of increasing heat to a hydrated compound results first in removal of physisorbed water, followed by removal of chemisorbed water, either concurrently or at higher temperatures which can also result in dehydroxylation. It should be understood that reference to this order of events is not meant to be limiting, since it may be possible that, for example, as physisorbed water approaches depletion removal of chemisorbed water may begin. Dehydration which results in dehydroxylation of a compound described herein as useful as a hemostatic agent (e.g., dehydroxylation of zeolite, dehydroxylation of a layered clay, e.g., kaolin) is not desirable to the extent such that the hemostatic activity of the compound is negatively affected (e.g., by one or more of significant reduction in pore diameter, chemical decomposition of the metal oxide framework of the compound, reduction of surface area, change in surface charge, change in the hydrophobic/hydrophilic character of the surface, and/or modification of the surface energy). For example, it may be desirable to avoid partial or complete dehydroxylation in preparation of zeolite (e.g., in preparation of dehydrated zeolite) or in preparation of layered clay, including kaolin, for use as a hemostatic agent. Thus, it is generally desirable to avoid significant vitrification of zeolite or of layered clay, including kaolin, during preparation for use as a hemostatic agent. Thus, the present disclosure specifically contemplates layered clay that is not vitrified, as well as zeolite that is not vitrified, as hemostatic agents.

"Hydrated" or "wet", which terms are used interchangeably herein, generally refers to a state of hydration of a compound (e.g., kaolin, zeolite, etc.) that is present when not subjected to a drying process to remove physisorbed water or chemisorbed water and/or when not maintained in a dry environment to prevent hydration (e.g., not maintained in a dry box and/or under vacuum, but rather maintained naturally maintained by the compound under ambient conditions of temperature and humidity). As will be readily appreciated by the ordinarily skilled artisan in the relevant field, ambient conditions of temperature and humidity can fluctuate depending on location and season, and thus is intended to encompass such fluctuations. It should be understood that a "hydrated" or "wet" compound can be provided in a composition without an aqueous carrier, e.g., without added water. The terms "hydrated" or "wet" in the context of a "hydrated compound" or "wet compound" refers to the state of hydration of the compound that is independent of the presence or absence of exogenous water, i.e., water that is not physisorbed water or chemisorbed water. Thus a "hydrated hemostatic agent" (e.g., a "hydrated" or "wet" layered clay, e.g., "hydrated kaolin" or "wet kaolin") can be provided in, for example, a dry (e.g., lyophilized) hemostatic composition, i.e., a hemostatic composition which does not contain exogenous water as a carrier.

"Partially hydrated" or "partially dehydrated" are used interchangeably herein to generally refer to a state of hydration of a compound (e.g., kaolin, zeolite, etc.) in which the compound contains less physisorbed and/or chemisorbed water than that present in a hydrated form of the same compound. For long term storage (e.g., greater than 12 hours, 24 hours, 3 days, 7 days, etc.), partially hydrated (or partially dehydrated) compounds thus must generally be maintained under conditions different from those of ambient conditions of temperature and humidity to avoid rehydration of the compound to a fully the hydrated stated.

"Dehydrated" or "dry" as used in the context of a hemostatic agent, and which terms are used interchangeably herein, generally refers to a state of hydration of a compound (e.g., kaolin, zeolite, etc.) that is decreased relative to a state of hydration that compound naturally maintains. For example, a dehydrated compound is one that has been subjected to a drying process to remove water (e.g., to at least partially remove physisorbed water and, optionally chemisorbed water, and may include substantially complete removal of physisorbed water with substantially complete or partial removal of chemisorbed water) and is maintained under appropriate dry conditions to inhibit rehydration (e.g., as in a sealed, water vapor resistant container). A fully dehydrated compound is one that has been subjected to a drying process that is sufficient to remove physisorbed and chemisorbed water without significant dehydroxylation of the compound, and which compound is maintained under conditions to avoid rehydration.

It should be noted that partially hydrated materials may be generated by subjecting the material to heat to remove some, but not all of the water content. In general, the distinction between a partially hydrated (or partially dehydrated) state and a fully dehydrated state of a composition can be described as the differences in the temperature to which the material was heated and maintenance of the material under conditions that avoid rehydration. In general, the temperature range(s) at which a partially hydrated material is produced versus a fully dehydrated material will vary, even between different zeolites or clays, which temperatures can be readily determined by the ordinarily skilled artisan by application of routine methods. For example, zeolite 5A is normally still partially hydrated even when heated to 250° C. (1-6%, by weight). The fully dehydrated form of zeolite 5A can be generated by heating the material to a temperature in the range of 300° C. and 500° C. However, severe heating of the material or heating the material so that the heated water vapor cannot readily escape (e.g., as in a "deep bed" sample) can cause dehydroxylation or structural changes in the material, and thus could be detrimental to the clotting properties of the material, should be avoided where possible so that a balance of a desired dehydration state and minimal dehydroxylation is achieved. For example, dehydroxylation of clays and zeolites can cause the material(s) to become less wettable, which can adversely affect the clotting properties of the material(s).

"Isoelectric point" or "IEP" as used herein refers to a pH at which the zeta-potential is about zero in an aqueous electrolyte such as 2 mM $CaCl_2$ or 2 mM NaCl.

The "zeta potential" refers to the surface charge density of a compound in aqueous suspension, which can be measured as a function of pH by an electrophoretic method using the Smoluchowski equation (see, e.g., Cocera et al. 1999 *Langmuir* 15:2230-2233). Unless specifically indicated otherwise, the zeta potential of a compound is measured in electrolyte such as simulated body fluid that mimics the $Ca^{2+}$ concentration in blood.

The term "isolated" means the compound is present in an environment other than that in which it is found in nature. "Isolated" is meant to include compounds that are within samples that are substantially enriched for the compound of interest and/or in which the compound of interest is partially or substantially purified.

As used herein, the term "purified" refers to a compound that is removed from its natural environment and is at least 60% free, at least 75% free, and most at least 90% free from other components with which it is naturally associated.

The terms "individual," "subject," "host," and "patient," used interchangeably herein, refer to any subject suitable for treatment, e.g., mammals, including, but not limited to, humans, simians, felines, canines, equines, bovines, mammalian farm animals, mammalian sport animals, and mammalian pets. Human subjects are of particular interest.

Before the present invention is further described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the exemplary methods and materials are now described. All publications mentioned herein are incorporated herein by reference to disclose and describe the methods and/or materials in connection with which the publications are cited.

It must be noted that as used herein and in the appended claims, the singular forms "a," "and," and "the" include plural referents unless the context clearly dictates otherwise. Thus, for example, reference to "a hemostatic agent" includes a plurality of such agents and reference to "the hemostatic agent" includes reference to one or more agents and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Moreover any positively recited element of the disclosure provides basis for a negative limitation to exclude that element from the claims.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DETAILED DESCRIPTION OF EXEMPLARY EMBODIMENTS

Exemplary embodiments of the present invention relate to hemostatic compositions which comprise kaolin as a hemostatic agent and, optionally, a second hemostatic agent such as zeolite, as well as methods as well as devices and methods of use to promote blood clotting.

Hemostatic Agents

Hemostatic agents for use in the hemostatic compositions and methods disclosed herein include a layered clay, such as kaolin, which can be optionally combined with zeolite. In certain embodiments, the layer clay-containing composition does not contain detectable zeolite. In other embodiments, the compositions comprise a zeolite composition and a layered clay in an admixture, wherein the composition includes layered clay other than that which may optionally be present as a binder in the zeolite composition.

As discussed in more detail below, a hemostatic agent can be selected according to various physical parameters which can influence parameters of blood clotting activity as well as the heat generated upon application of the hemostatic agent to a subject. For example, agent can be selected according to physical characteristics (e.g., crystalline form/shape, porosity, surface area, silicon:aluminum ratio, surface charge (e.g., as estimated by isoelectric point), and the like) and modifications (e.g., cation-exchanged, addition of inorganic salts, hydration state, and the like).

Properties of exemplary compounds (e.g., kaolin and zeolite) contemplated as hemostatic agents are described in further detail below Layered Clays Layered clays (also referred to herein as "clays", which term is used interchangeably with "layered clay") refers to a genus of aluminosilicate compounds that, structurally, are composed of a layered crystalline structure and may be subject to shrinking and swelling as water is absorbed and removed between the layers. Exemplary layered clays useful as hemostatic agents include, but are not limited to, clays in the kaolin group ($Al_2Si_2O_5(OH)_4$, referred to herein interchangeably as "kaolin" or "kaolinite"); clays in the smectite group (referred to herein as "a smectite"), including montmorillonite (($Na,Ca)_{0.33}(Al,Mg)_2(Si_4O_{10})(OH)_2.nH_2O$) and saponite ((½$Ca,Na)_{0.33}(Mg,Fe^{+2})_3(Si,Al)_4O_{10}(OH)_2.4H_2O$.); palygorskite (also known as attapulgite), and sepiolite. (both $Si_{12})(Mg_8)O_{30}(OH)_6(OH_2)_4.8H_2O$). Optionally, the layered clay is other than palygorskite, particularly when in provided in a composition in combination with a zeolite.

In general, layered clays for use as a hemostatic agent can be selected based on various physical parameters that provide a desired property (e.g., clotting time, clotting rate, clot strength, heat of hydration) of the final hemostatic composition (e.g., a hemostatic composition containing kaolin without zeolite, or containing both kaolin and zeolite). Exemplary characteristics of kaolin of are described in more detail below.

Layered clays for use in the disclosed hemostatic compositions can be naturally occurring or synthetically produced. For example, several synthetically produced smectite clays are available. Where available, synthetic clays may be desirable due to the ease in control purity and composition. Exemplary synthetic Smectite clays include, but are not limited to Laponite RD from Southern Clay Products, Hectorite Optigel SH from Sud-Chemie Rheologicals, synthetic Saponite, Sumecton, from Kunimine Industries, synthetic Montmorillonite Barasym SSM-100. Numerous varieties of naturally occurring layered clays are found as deposits in sedimentary environments as well as in other places. For example, naturally occurring kaolins that can be useful in the hemostatic compositions and methods disclosed herein include, but are not limited to, K—Ga-1 and K—Ga-2 (names defined by Source Minerals Repository). Naturally occurring montmorillonites that can be useful in the hemostatic compositions and methods disclosed herein include, but are not limited to, montmorillonite, SWy-1 and Stx-1 (names defined by Source Minerals Repository). Naturally occurring saponites that can be useful in the hemostatic compositions and methods disclosed herein include, but are not limited to, SapCa-2 (Source Minerals Repository). Layered clays for use in the hemostatic compositions and methods disclosed herein can be of any structural type compatible with hemostatic activity of the compound.

Other properties of layered clays which can be used in the hemostatic compositions and methods disclosed herein are exemplified below. In general, layered clays can be selected based on physical parameters that provide a desired property (e.g., clotting time, clotting rate, clot strength, heat of hydration) of the final hemostatic composition (e.g., a hemostatic composition containing a layered clay (e.g., kaolin) and zeolite).

Surface Charge

The surface charge of a material in a given medium (e.g., blood, including whole blood, or simulated body fluid), can be selected so as to provide for a desired hemostatic activity. As illustrated in the Examples section below, surface charge can be an influential parameter in determining the hemostatic activity of the compound. The zeta potential of a material reflects the magnitude and sign of a surface charge in a given medium can be experimentally determined by measuring the electrophoretic mobility of the particles, and calculated using the Smoluchowski equation (see, e.g., Cocera et al. 1999 Langmuir 15:2230-2233).

Figure 3:
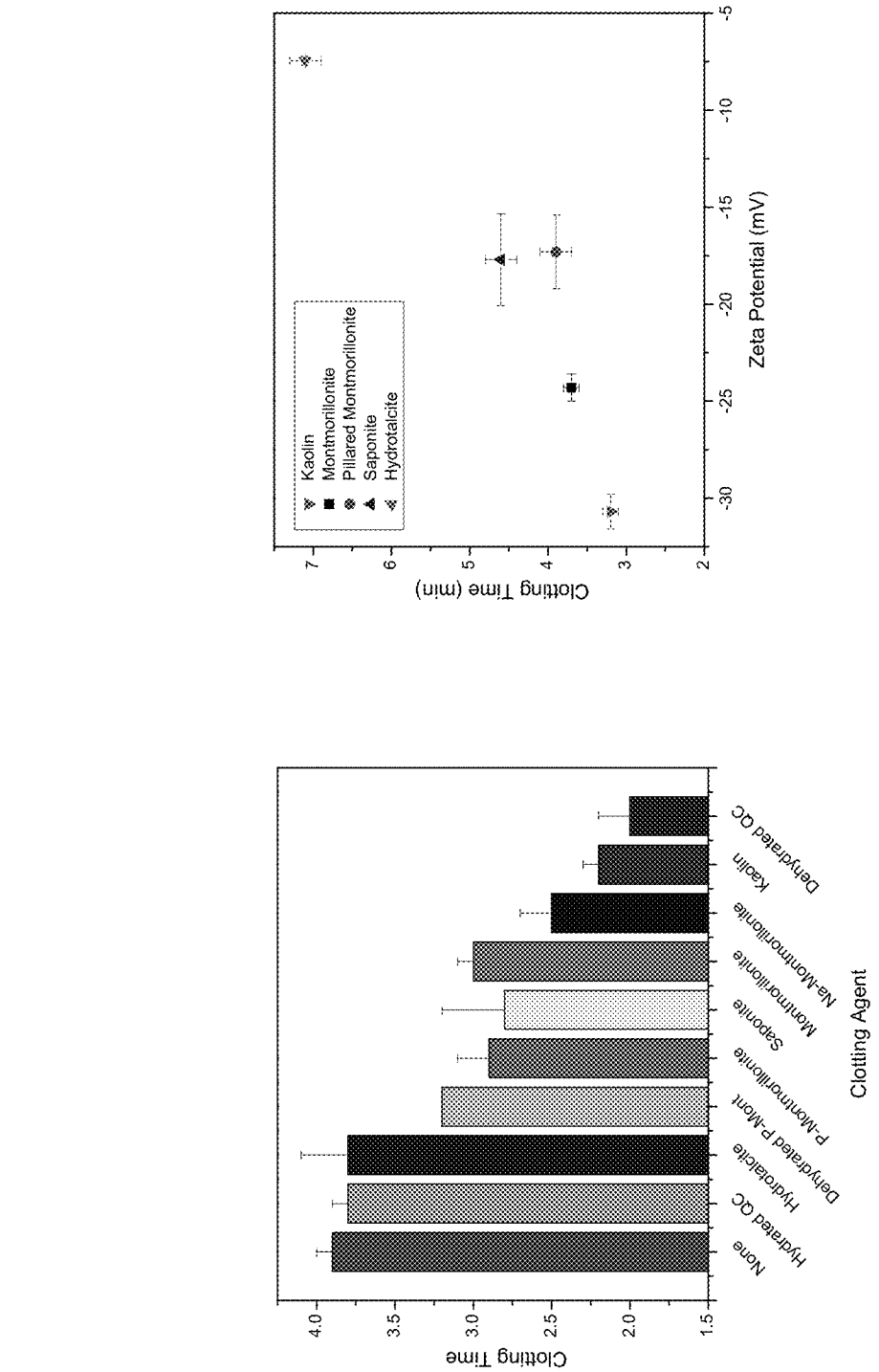
FIG. 3 is a set of graphs showing the effect of layered clays upon clotting rate (left panel) and the zeta potential of the layered clays tested (right panel).

As discussed in the Examples section below, the zeta potential of a layered clay immersed in Simulated Body Fluid (SBF) directly correlated with clotting activity. As illustrated in the Examples below, clays with increasingly negative zeta potential exhibited increased efficacy in promoting reduced clotting time. For example, hydrotalcite clay, which exhibited the lowest efficacy in promoting clotting (FIG. 3, left panel) also exhibited the least negative zeta potential (−7.5 millivolts (mV)) in SBF (FIG. 3 right panel). The zeta potential of kaolin in SBF was the most negative of the clays examined (−30.7 mV) (FIG. 3, right panel), and was also the most active clotting agent (FIG. 3, left panel). Clays exhibiting intermediate zeta potentials in SBF also exhibited intermediate clotting activities. Thus, a layered clay for use as a hemostatic agent can be selected so as to have a desired hemostatic activity. For example, the layered clay can have a zeta potential of at least −10 mV or greater, at least −15 mV or greater, at least −20 mV or greater, at least −25 mV or greater, or at least −30 mV or greater, where in the context of a negative zeta potential the term "greater" indicates the zeta potential is a larger negative value.

Wettability

The wettability of the layered clay can also be selected for characteristics favorable to use as a hemostatic agent. The wettability of a material is defined as the ability of the material to be readily dispersed in water or biological fluids (e.g., whole blood or plasma). The hemocompatibility of blood-interfacing materials can be determined by measuring the contact angle/wettability of a surface and by categorizing materials based on surface energy. Materials that are more wettable have a higher surface energy, as determined by contact angle measurements. Increased wettability and higher surface energy can positively affect activity as a procoagulant. (Vogler et al. (1995) "Contact Activation of the Plasma Coagulation Cascade." *Journal of Biomedical Materials Research* 16:1005-1016; Ko, et al. (1981) "Characterization of Hydrophilic-Hydrophobic Polymeric Surfaces by Contact Angle Measurements." *J. Colloid Interface Sci.* 82:25-37; Israelachvili, *Intermolecular and Surface Forces*. 2nd ed.; Elsevier Academic Press: London, 1992.)

Si:Al Ratio

The layered clay can be of any appropriate molar ratio of silicon to aluminum (Si:Al), with the proviso that the Si:Al ratio is selected so as that the clay exhibits a desired hemostatic activity. Si:Al ratios can be tailored in synthetic smectite clays. For example, synthetic saponites have been synthesized successfully with Si/Al ratios of 5.67, 7.89, 12.3, and 39.0. (Vogels et al. (2005) Synthesis and Characterization of Saponite Clays. *American Minerologist* 90:931-944). The XRD patterns of these clays are not substantially changed by the variation in Si/Al ratios, but it can reasonably be assumed that the layer charge, and thus swelling capacity and cation exchange capacity will change based on this change of composition.

As illustrated in the Examples below for zeolite, and without being held to theory, the Si:Al ratio of a material can affect the clotting time facilitated by the compound. Thus, as with other physical parameters of layered clay, the Si:Al ratio can be selected according to the desired hemostatic properties of the final hemostatic composition. Exemplary Si:Al ratios for layered clay include 1, 1.5, 2, 2.5, 3, 3.5, 4, 4.5, 5, 5.5, 6, 7, 8, 9, 10, 15, 25, and 30. Further exemplary Si:Al ratios for layered clay include 1 or greater, 1.5 or greater, 2.0 or greater, 2.5 or greater, with a Si:Al of from 1 to 40; 1 to 30; 1.5 to 40; 1.5 to 30; 2.0 to 40; 2.5 to 40.

Morphology of Aggregates of Layered Clay

The macrostructure of the layered clay can take a variety of forms, with the proviso that such should be compatible with providing for activity as a hemostatic agent. For example, layered clays can be provided as irregularly-shaped granular material which can contain aggregates of up to 50 micrometers.

When provided as an aggregate, the morphology of the layered clay can be selected so as to provide for parameters which can prove beneficial to hemostatic activity of the compound. For example, the morphology of the layered clay aggregate in terms of macrostructure, surface area and/or pore size can be selected to provide an increase surface area and display of a negatively charged surface of the layered clay so as to facilitate contact of blood and blood components with the layered clay.

For example, the surface area of layered clay for use in the compositions and methods disclosed herein can be selected so as to be optimal for hemostatic activity of layered clay or a hemostatic composition containing layered clay (e.g., kaolin combined with zeolite). For example, the layered clay can have a surface area of from 5 $m^2/g$ to 1,500 $m^2/g$, 10 $m^2/g$ to 1,000 $m^2/g$, 15 $m^2/g$ to 900 $m^2/g$, 20 $m^2/g$ to 800 $m^2/g$, 25 $m^2/g$ to 750 $m^2/g$, 30 $m^2/g$ to 700 $m^2/g$, 30 $m^2/g$ to 650 $m^2/g$, 30 $m^2/g$ to 600 $m^2/g$, 45 $m^2/g$ to 725 $m^2/g$, and the like, with layered clay having a surface area of from 10 $m^2/g$ to 725 $m^2/g$ being exemplary.

The surface area of aggregates of layered clay can be increased by selection of or production of layered clay aggregates having increased porosity. Layered clay aggregates can have a range of porosities, including, but not necessarily limited to nanoporous (e.g., having pores of from 3 angstroms to 10 angstroms, usually from 2 angstroms to 5 angstroms), microporous, (less than 2 nm), mesoporous (e.g., having pores of from 2 nm to 50 nm in diameter), macroporous (e.g., having pores greater than 50 nm diameter).

Morphology and particle size of layered clays can be selected to as to provide for a desired blood component-accessible external surface area. As exemplified in the working examples below (see, e.g., Example 8), accessible external surface area can be modified through selection of morphology and size. For example, where the layered clay exhibits a morphology having relatively less accessible surface area, it may be desirable to decrease the average particle size of the layered clay, e.g., to less than 1 micron to provide layered clay particles having an average particle size in the submicron range.

Cation-Exchanged Layered Clay

Layered clay may be ion-exchanged to include or replace a cation, for example, calcium, sodium, potassium, silver, or magnesium, or any combination of thereof. A compound having a cation substituted or in addition to a naturally occurring ion of the compound is referred to herein as a "cation-exchanged" compound. A material having a cation (e.g., calcium) that can be released upon contact with an aqueous medium (e.g., water, blood, plasma, especially blood or plasma) is referred to as a "cation-loaded" compound (e.g., a "calcium loaded" compound). Cation-loaded compound can be produced by cation-exchange and/or can contain the cation naturally.

Production of a cation-exchanged compound can be accomplished according to methods known in the art. For example, the layered clay can be immersed in a 0.1 M to 1 M aqueous cation exchanging solution of one or more alkali, alkaline earth, and/or transition metal cations (e.g., sodium chloride, potassium chloride, calcium chloride, magnesium sulfate, zinc chloride, or silver nitrate) for a sufficient number of times and for sufficient internals (e.g., three thirty minute intervals). The exchanging solution is normally removed in between each successive washing. After rinsing with deionized water to facilitate removal of any soluble ions not incorporated with the layered clay material, the ion exchanged material may then subjected to a dehydrating process as desired (e.g., heated to at least 100° C. under vacuum ($10^{-3}$ tort) for 12 hours) to remove excess water. It is appreciated that layered clays differ in cation exchange capacity. For example, kaolin has a relatively lower cation exchange capacity (2.0 meq/100 g), while smecites have a relatively higher cation exchange capacity (e.g., 70 meq/100 g).

In addition or alternatively, cation-exchanged layered clay can be mixed with neutral inorganic salts like calcium chloride, aluminum sulfate, and silver nitrate.

Effect Upon Calcium Concentration of Physiological Aqueous Environment

Layered clays which remove relatively less $Ca^{2+}$ from the aqueous environment in which the layered clay is present (e.g., in simulated body fluid (SBF)) facilitate a faster clotting time compared to layered clays that remove relatively more $Ca^{2+}$ in the solution. Calcium ion depletion properties of layered clays can be independent of other layered clay properties (e.g., independent of surface potential) (see, e.g., Example 4). Thus, layered clays that cause, less than 30 ppm decrease in $Ca^{2+}$ concentration (referred to here as "$[Ca^{2+}]$"), less than 20 ppm decrease in $[Ca^{2+}]$, less than 10 ppm decrease in $[Ca^{2+}]$, or no significant or detectable change in $[Ca^{2+}]$ when exposed to an aqueous environment having a physiologically relevant calcium concentration, which for purposes herein is on the order of 1 mM to 2.5 mM $Ca^{2+}$ (where blood plasma is about 1.3 mM $Ca^{2+}$, and simulated body fluid is about 1.6 mM $Ca^{2+}$)5 are of particular interest as hemostatic agents according to the present disclosure. The calcium-depleting effect of a layered clay can be modulated by "loading" the layered clay with calcium (e.g., through cation exchange with a calcium salt as described above).

Inorganic Salts

Layered clay can be provided in combination with one or more inorganic salt. Examples of inorganic salts include, but are not necessarily limited to, calcium, silver, sodium, potassium, zinc, magnesium, and ammonium. Exemplary salts include sulfate, oxide, halo (e.g., chloride, bromide), nitrate, phosphate, acetate, and citrate salts. Specific exemplary salts include CaO, $CaCl_2$, $AgNO_3$, $Ca(NO_3)_2$, $Mg(NO_3)_2$, $Ag(NO_3)_2$, $NH_4NO_3$, AgCl, $Ag_2O$, zinc acetate, magnesium acetate, calcium citrate, zinc citrate, magnesium citrate, magnesium chloride, zinc chloride, calcium acetate, and calcium phosphate. In an exemplary method, an inorganic salt(s) is blended with layered clay. Inorganic salts can comprise between 0.001% and 50% by weight of the composite.

Hydration

Where desired in some embodiments, the moisture content of the layered clay in the hemostatic composition can be adjusted, e.g., by drying, re-hydrating, or a combination of drying and re-hydrating the layered clay such that the layered clay has a specific moisture content. Such may be particularly desired where the layered clay has a high swelling capacity, such that the layered clay contain a significantly high water content (e.g., 10%, 20% or 30% by weight water). Exemplary moisture contents of layered clays contemplated herein include hydrated and/or partially dehydrated clays having a moisture of from 0.5 wt % to 30 wt %, 1 wt % to 25 wt %, 5 wt % to 20 wt %, 10 wt % to 15 wt %, or 30 wt % or more. Where the layered clay is to be combined in a mixture with an least partially dehydrated zeolite in a hemostatic composition, the moisture content of the layered clay should be selected to avoid transfer of water to the at least partially dehydrated zeolite in a manner that would significantly adversely affect the hemostatic activity of the hemostatic composition.

Drying of layered clay to provide for a desired hydration level may be effected by the application of heat. Heating can be accomplished so as to drive off adsorbed water bound in the crystalline structure is driven off without altering the structure itself or detracting from its integrity. The dried layered clay may then be re-hydrated. Alternatively, the drying process can be stopped before the material is completely dehydrated. The final hydration of the material can be controlled by monitoring and controlling the temperature of zones of a drying apparatus in which the material is dried.

In another exemplary method, layered clay is partially hydrated by storage in a humidity chamber for a sufficient period (e.g., from 1 day to two weeks in a humidity chamber regulated at 0 to 80% natural humidity relative to pure phase water). The extent of hydration can be controlled by the duration and humidity setting of the storage conditions. Pre-hydration can also be achieved by mixing a known quantity of water and layered clay in a sealed container. The sealed container can be heated to a suitable temperature (e.g., at least 60° C.) and slowly re-cooled to evenly distribute the water among the layered clay particles.

The partially hydrated layered clay is then maintained in a container to avoid rehydration of the material. Where the partially hydrated layered clay is to be stored for a extended period of time, it may be desirable to maintain the material in the container under vacuum to avoid hydration by air in the packaging. For example, the material can be sealed in a mylar foil bag (e.g., under vacuum) until use.

Binders and Other Components

In some embodiments, the layered clay is provided in a bound form in which layered clay particle are held together by a binder or in an unbound form. It should be noted that reference to an "unbound" compound, such as in the context of "unbound" layered clay (e.g., unbound kaolin) indicates that the layered clay composition does not include a binder. When present, the binder can be any suitable material compatible with the hemostatic compositions described herein and their methods of use. For example the binder can be clay-based, and can be a natural or modified clay, or may be polymer-based, such as polyvinyl alcohol. Exemplary clays include, but are not limited to, kaolin, montmorillonite, saponite, bentonite, palygorskite (also known as attapulgite), combinations of the foregoing, and the like, with the proviso that the binder is a compound different from that of the hemostatic agent. Modified clays such as polyorganosilcate graft polymers may also be suitable. Binders can be used to control morphology, and can optionally act as an additional hemostatic agent.

Zeolite

Zeolites are high surface area porous aluminosilicates. Chemically, zeolites are similar to layered clays described above in that both are aluminosilicates. However, zeolites differ from layered clays in their crystalline structure. As noted above, layered clays have a layered crystalline structure and are subject to shrinking and swelling as water is absorbed and removed between the layers. In contrast, zeolites have a rigid, 3-dimensional crystalline structure consisting of a network of interconnected tunnels and cages (similar to a honeycomb). Water moves freely in and out of these pores but the zeolite framework remains rigid. The pore and channel sizes of zeolite are nearly uniform, which allows the crystal to act as a molecular sieve. The porous zeolite is host to water molecules and ions of, for example, potassium, calcium, and/or other positively charged guest ions of a size and charge compatible with the zeolite structural framework. Such ions facilitate the "sieving" property of zeolite.

In general, the oxide structural framework is composed of tetrahedral units of $SiO_4$ and $AlO_4$ linked together through shared oxygen atoms. Each Al position in the oxide framework induces a negative charge that can be counterbalanced by counter-cations that reside in the open porous network Coulombically bound to the oxide framework. When zeolites are extensively dehydrated, they are capable of rapidly absorbing water, which can be up to about 30% by weight of the compound. Rehydration of a zeolite is an exothermic, or heat releasing reaction, and can predictability warm a known volume of liquid. Additionally, zeolites have an added property that allows for ionic exchange of the compound's cations with a solution in contact with the zeolite.

As used herein, the term "zeolite" refers to a crystalline form of aluminosilicate, also referred to as a "molecular sieve", which can include compounds of different porosity and surface area, silicon:aluminum (Si:Al) ratios, as well as several different cation-containing species including sodium and calcium moieties. In general, zeolite useful as a hemostatic agent include those having a structural framework (e.g., pore size and/or surface area) and silicon:aluminum ratio to provide for a desired effect in decreasing clotting time, increasing clotting rate, and/or increasing clot strength when provided in a hemostatic composition either as the only hemostatic agent or in combination with a second hemostatic agent, such a kaolin.

Zeolites for use in the disclosed hemostatic compositions can be naturally occurring or synthetically produced. Numerous varieties of naturally occurring zeolites are found as deposits in sedimentary environments as well as in other places. Naturally occurring zeolites that can be useful in the hemostatic compositions and methods disclosed herein include, but are not limited to, analcite, chabazite, heulandite, natrolite, stilbite, and thomosonite. Synthetically produced zeolites that can also find use in the hemostatic compositions and methods described herein can generally be produced by processes in which rare earth oxides are substituted by silicates, alumina, or alumina in combination with alkali or alkaline earth metal oxides.

Zeolites for use in the hemostatic compositions and methods disclosed herein can be of any structural type compatible with hemostatic activity of the compound. Exemplary zeolites for use as hemostatic agents in the compositions and methods disclosed herein include one or more of the following types A (e.g., 5A), Y, beta, mordenite, and/or ZSM-5. In addition, the zeolite can be a mixture of zeolites of different types, e.g., a mixture of two, three or more of zeolite types A, Y, Beta, mordenite, and ZSM-5.

In certain embodiments, the zeolite is an "A-type" crystal or a "Y type" crystal. An exemplary molecular structure of the zeolite is of an "A-type" crystal form. As used herein, the term "A-type crystal" is intended to indicate a crystal having a cubic crystalline structure and round holes. In another exemplary embodiment, the molecular structure of the zeolite is of a "Y-type" crystal form. Y-Type zeolites are generally characterized by an FAU framework structure of sodalite cages connected by six-membered rings, where the sodalite cages are arranged to form a "supercage" with a diameter of 12 Angstroms and an opening of 8 Angstroms. The sodalite cages that make up the supercage have a smaller diameter of 4-5 Angstroms. The framework of Y-Type zeolites is thus composed of alternating silica and alumina tetrahedra that are joined by oxygen atoms.

Other properties of zeolite which can be used in the hemostatic compositions and methods disclosed herein are exemplified below. In general, zeolite can be selected based on physical parameters that provide a desired property (e.g., clotting time, clotting rate, clot strength, heat of hydration) of the final hemostatic composition (e.g., a hemostatic composition containing kaolin and zeolite).

Pore Size

Zeolite for use in hemostatic compositions and methods disclosed herein can have a range of porosities, including, but not necessarily limited to nanoporous (e.g., having pores of from 3 angstroms to 10 angstroms, usually from 2 angstroms to 5 angstroms), microporous, having pores less than 2 nm, mesoporous (e.g., having pores of from 2 nm to 50 nm in diameter), macroporous (e.g., having pores greater than 50 nm in diameter). It will be readily appreciated that increasing pore size up to a certain level provides for increased protein-accessible surface area of the material. In one embodiment, the zeolite is microporous.

Surface Area

The surface area of zeolite for use in the compositions and methods disclosed herein can be selected so as to be optimal for hemostatic activity of zeolite, particularly when combined with kaolin. For example, the zeolite can have a surface area of from 100 $m^2/g$ to 1,500 $m^2/g$, 100 $m^2/g$ to 1,000 $m^2/g$, 100 $m^2/g$ to 900 $m^2/g$, 200 $m^2/g$ to 800 $m^2/g$, 300 $m^2/g$ to 750 $m^2/g$, 300 $m^2/g$ to 700 $m^2/g$, 300 $m^2/g$ to 650 $m^2/g$, 300 $m^2/g$ to 600 $m^2/g$, 450 $m^2/g$ to 725 $m^2/g$, and the like. One study reports the surface area of zeolite 5A is 700 $m^2/g$-800 $m^2/g$.

Wettability

The wettability of zeolite can also affect its characteristics as a hemostatic agent. As discussed above, the wettability of a material is defined as the ability of the material to be readily dispersed in water or biological fluids (e.g., whole blood or plasma), and can be determined by measuring the contact angle/wettability of a surface and by categorizing materials based on surface energy. Materials that are more wettable have a higher surface energy, as determined by contact angle measurements. Increased wettability and higher surface energy can positively affect activity as a procoagulant. (Vogler et al. (1995) "Contact Activation of the Plasma Coagulation Cascade." *Journal of Biomedical Materials Research* 16:1005-1016; Ko, et al. (1981) "Characterization of Hydrophilic-Hydrophobic Polymeric Surfaces by Contact Angle Measurements." *J. Colloid Interface Sci.* 82:25-37; Israelachvili, *Intermolecular and Surface Forces.* 2nd ed.; Elsevier Academic Press: London, 1992.)

Si:Al Ratio

The zeolite can be of any appropriate molar ratio of silicon to aluminum (Si:Al), with the proviso that the Si:Al ratio is selected so as that the zeolite exhibits a desired hemostatic activity. As illustrated in the Examples below, and without being held to theory, as the Si:Al ratio increase, the clotting time facilitated by zeolite also tends to increase. This is most likely due to the increased presence of tetrahedrally coordinated aluminum in the framework structure of zeolites with low Si:Al ratios, which increases the overall negative charge of the zeolite. Thus, as with other physical parameters of zeolite, Si:Al ratio should be selected according to the desired hemostatic properties of the final hemostatic composition. Exemplary Si:Al ratios for zeolite include 1, 1.5, 2, 2.5, 3, 3.5, 4, 4.5, 5, 5.5, 6, 7, 8, 9, 10, 15, 25, 30, 35 and 40. It should be noted that some zeolites, such as ZSM-5 and Beta zeolites, can exhibit a wide range of Si:Al ratios, up to and including, infinity, i.e., no detectable aluminum in the framework. Replacement of aluminum in the zeolite framework with silicon would, as it approaches a purely siliceous zeolite (e.g., such as silicalite in the case of ZSM-5) that can exhibit reduced activity in promoting blood clotting, e.g., due to the absence of a negative framework charge and the hydrophobic nature (non-wettable) of the material.

Cation-Exchanged Zeolite

The zeolite may be ion-exchanged to include a cation, for example, calcium, sodium, potassium, silver, or magnesium, or any combination of thereof, to produce a cation-loaded zeolite of one or more desired cations (e.g., calcium-loaded zeolite). Production of a cation-loaded zeolite can be accomplished according to methods known in the art. For example, the zeolite can be immersed in a 0.1 M to 1 M aqueous cation exchanging solution of one or more alkali, alkaline earth, and/or transition metal cations (e.g., lithium chloride, sodium chloride, potassium chloride, strontium nitrate, barium nitrate, ammonium chloride, silver nitrate, zinc chloride) for a sufficient number of times and for sufficient internals (e.g., three thirty minute intervals). The exchanging solution is removed in between each successive washing. After rinsing with deionized water to facilitate removal of any soluble ions not incorporated with the zeolite material, the ion exchanged material is then subjected to a dehydrating process as desired (e.g., heated to at least 100° C. under vacuum ($10^{-3}$ tort) for 12 hours) to remove water bound inside the zeolite. In addition or alternatively, ion exchanged zeolite can be mixed with neutral inorganic salts like calcium chloride, aluminum sulfate, and silver nitrate and dehydrated to remove water. As needed, the material can then be maintained in an environment to avoid rehydration (e.g., by sealing in a mylar foil bag)

until use. In one embodiment, the hemostatic agent is a calcium loaded zeolite Linde type A that is ion exchanged with an aqueous solution of alkali, alkaline earth, and/or transition metal cations to provide specific ion formulations.

Inorganic Salts

Zeolite can be provided in combination with one or more inorganic salt. Examples of inorganic salts include, but are not necessarily limited to, a divalent ion of zinc, copper, magnesium, calcium, nickel, and ammonium, and silver. Exemplary salts include sulfate, oxide, halo (e.g., chloride, bromide), nitrate, phosphate, acetate, and citrate salts. Specific exemplary salts include CaO, $CaCl_2$, $AgNO_3$, $Ca(NO_3)_2$, $Mg(NO_3)_2$, $Ag(NO_3)_2$, $NH_4NO_3$, AgCl, $Ag_2O$, zinc acetate, magnesium acetate, calcium citrate, zinc citrate, magnesium citrate, magnesium chloride, zinc chloride, calcium acetate, and calcium phosphate. In an exemplary method, an inorganic salt(s) is blended with zeolite when it is in a dehydrated state. Inorganic salts can comprise between 0.001% and 50% by weight of the composite.

Hydration

In some embodiments, the moisture content of the zeolite in the hemostatic composition is adjusted by drying, re-hydrating, or a combination of drying and re-hydrating the zeolite such that the zeolite has a specific moisture content. A fully hydrated zeolite ("wet" zeolite) has a moisture content of about 15 or 20 weight percent (wt. %) up to about 30 wt %. The water content can be adjusted to a desired water content that provides for a desired heat release upon rehydration, particularly in the context of kaolin in a hemostatic composition also containing kaolin as described herein. Exemplary moisture contents of partially hydrated zeolite include, but are not limited to, from 0.5 wt % to 30 wt %, 1 wt % to 20 wt %, 1 wt % to 15 wt %, 1.5 wt % to 25 wt %, 1.5 wt % to 10 wt %, 2 wt % to 8 wt %, 3 wt % to 7 wt %, 4 wt % to 6 wt %, 0.5 wt % to 5 wt %, 1 wt % to 4.5 wt %, 1.5 wt % to 4 wt %, 2 wt % to 5 wt %, 3 wt % to 7 wt %, and the like. It is appreciated that the hydration capacity of a zeolite can depend upon the framework structure of the zeolite, and thus can vary by zeolite type.

In one embodiment, the zeolite used in the hemostatic composition in combination with kaolin is dehydrated or "dry", which includes zeolites dried to remove physisorbed and chemisorbed water to a level that is compatible with drying without significant dehydroxylation. As discussed in the Examples below, combination of wet kaolin and dry zeolite can provide for a hemostatic composition having a balance of heat release, clotting time, clotting rate, and clot strengths that can prove beneficial in methods of controlling bleeding, e.g., such hemostatic composition can provide for rapid clotting with a heat of hydration that promotes clotting, but reduces risk of burning the subject. Zeolite that is dehydrated to remove water while avoiding significant dehydroxylation may have a moisture content of from 1 wt % to 6 wt % water, where fully dehydrated zeolite may have a moisture content of 1 wt % water or less.

Drying of the zeolite may be effected by the application of heat. Heating can be accomplished so as to drive off adsorbed water bound in the crystalline structure is driven off without altering the structure itself or detracting from its integrity. The dried zeolite may then be re-hydrated. Alternatively, the drying process can be stopped before the material is completely dehydrated. The final hydration of the material can be controlled by monitoring and controlling the temperature of zones of a drying apparatus in which the material is dried.

In another exemplary method, zeolite is partially hydrated by storage in a humidity chamber for a sufficient period (e.g., from 1 day to two weeks in a humidity chamber regulated at 0 to 80% natural humidity relative to pure phase water). The extent of hydration can be controlled by the duration and humidity setting of the storage conditions. Prehydration can also be achieved by mixing a known quantity of water and zeolite in a sealed container. The sealed container can be heated to a suitable temperature (e.g., at least 60° C.) and slowly re-cooled to evenly distribute the water among the zeolite particles.

The partially hydrated zeolite is then maintained in a container to avoid rehydration of the material. Where the partially hydrated zeolite is to be stored for a extended period of time, it may be desirable to maintain the material in the container under vacuum to avoid hydration by air in the packaging. For example, the material can be sealed in a mylar foil bag (e.g., under vacuum) until use.

In general, hydrated or partially hydrated zeolite generates less heat upon contact with blood than zeolite that is partially or fully dehydrated, respectively. In general, the heat of hydration is inversely proportional to the moisture content of zeolite. Therefore, for example, a zeolite hydrated to a moisture content of 4 wt. % will generate measurably less heat than a zeolite that has been fully dehydrated to less than 0.1 wt. %. However, regardless of hydration state, the zeolite becomes fully-saturated with water upon application to a bleeding wound. Thus, use of a hydrated or partially dehydrated zeolite exhibits reduced exothermic effects as a result of a reduced total enthalpy of rehydration, and thus reduced heat transfer to a wound than a fully dehydrated zeolite.

Macrostructure

The macrostructure of the zeolite can take a variety of forms, with the proviso that such should be compatible with providing for activity as a hemostatic agent. For example, in one embodiment, the zeolite comprises irregularly-shaped granular material that is prepared by grinding larger particles and then selecting material that will pass through a 16 mesh sieve screen but will not pass through a 40 mesh sieve screen. The resulting zeolite is a composition of irregular granules that range in size from 0.4 millimeters (mm) in diameter to 0.8 mm in diameter Binders and Other Components In some embodiments, zeolite is provided in a bound form in which zeolite particle are held together by a binder. It should be noted that reference to an "unbound" compound, such as in the context of "unbound" zeolite indicates that the zeolite composition does not include a binder. When present, the binder can be any suitable material compatible with the hemostatic compositions described herein and their methods of use. For example the binder can be clay-based, and can be a natural or modified clay. Exemplary clays include, but are not limited to, kaolin, kaolinite, bentonite, montmorillonite, palygorskite, saponite, combinations of the foregoing, and the like. Modified clays such as polyorganosilcate graft polymers may also be suitable. In some embodiments, the binder used with bound zeolite is other than kaolin or other than kaolinite.

Hemostatic Compositions

Hemostatic compositions of the present disclosure can include one or more layered clays as hemostatic agents as disclosed herein, and may optionally include a zeolite. In general, hemostatic compositions of the present disclosure include at least a layered clay hemostatic agent as described above, and may further include a combination of a layered clay as a first hemostatic agent and a zeolite as a second hemostatic agent. In one embodiment of interest, the hemostatic composition includes a wet layered clay (e.g., wet kaolin) and zeolite, wherein the zeolite is at least partially dehydrated.

Where the hemostatic composition is composed of more than one hemostatic agent, the hemostatic agents may be provided in a variety of formats. For example, the hemostatic agents of the hemostatic compositions may be provided as a mixture (e.g., blended or admixed), may be provided as a coating of a substrate (e.g., where one or both of the hemostatic agents is provided as a coating adhered to a substrate), or may be provided in a single package in the same or separate compartments of the package.

In general, hemostatic compositions can be provided as a sterile composition, and as such are generally provided in a sealed, sterile container which maintains the sterility of the hemostatic composition until use. Where one or more of the hemostatic agents are partially hydrated, the container can further provide for maintenance of the hydration state of the partially hydrated hemostatic agent, e.g., through use of materials that provide a water vapor-resistant barrier (e.g., mylar).

In some embodiments, the hemostatic composition does not contain added water, i.e., does not contain water other than water bound to the compound such as physisorbed or chemisorbed water. Instead, the hemostatic composition can be provided as a "dry", granular material (e.g., which can be poured directly into a bleeding wound).

Relative Amounts of Hemostatic Agents in Hemostatic Compositions

Where the hemostatic composition includes two or more hemostatic agents, these hemostatic agents can be provided at different ratios in the hemostatic composition, as may be selected for the desired hemostatic activity, and particularly as for a desired heat of hydration of the hemostatic composition. The relative amounts of the hemostatic agents can thus provide for "tuning" of a desired activity of the hemostatic composition.

For example, where the hemostatic composition includes a layered clay (e.g., kaolin) and a zeolite, exemplary hemostatic compositions include those having a layered clay:zeolite ratio (weight:weight) in ranges from 1:1 to 7:5, 1.5:1 to 7:4, 1.5:1 to 7:3, 1.5:1 to 7:2, 1.5:1 to 7:1, 1.5:1 to 6:5, 1.5:1 to 6:1, 1.5:1 to 5:3, 1.5:1 to 5:2, 1.5:1 to 5:1, 1.5:1 to 4:3, 1.5:1 to 4:1, 1.5:1 to 3:2, 1.5:1 to 3:1, 1.5:1 to 7:2, to 2:1, and the like, including 2:3, 1:3, 1.5:1, 2:1, 3:1, 3:2, 4:1, 4:3, 5:1, 5:2, 5:3, 6:1, 6:5, 7:1, 7:2, 7:3, 7:4, 7:5 and the like. Ratios of layered clay: zeolite of greater than 1:1, 1.5:1 or greater, 2:1 or greater, 2.5:1 or greater, 3:1 or greater, 3.5:1 or greater, 4:1 or greater, 4:3 or greater, 5:1 or greater, 5.5:1 or greater, 6:1 or greater, 6.5:1 or greater, 7:1 or greater, 7.5:1 or greater are also contemplated herein.

Further exemplary hemostatic compositions having a layered clay (e.g., kaolin) and a zeolite contemplated herein include those in which the layered clay is present at greater than 50 wt %, 55 wt % or great, 60 wt % or greater, 65 wt % or greater, 70 wt % or greater, 75 wt % or greater, 80 wt % or greater, 95 wt % or greater, and up to 100 wt %, where wt % in this context indicates the weight of layered clay expressed as a percent of total combined weight of layered clay and zeolite.

Hemostatic compositions containing kaolin:zeolite, smectite:zeolite, montmorillonite:zeolite, saponite:zeolite, palygorskite:zeolite, and/or sepiolite:zeolite at these ratios and weight percentages of total layered clay and zeolite are exemplary of the hemostatic compositions of the present disclosure. In some embodiments, the hemostatic composition does not contain a layered clay other than at least one of kaolin, smectite, montmorillonite, saponite, palygorskite and sepiolite. In other embodiments, the hemostatic composition contains combinations of two or more of kaolin, smectite, montmorillonite, saponite, palygorskite and sepiolite. For example, the hemostatic composition can include a combination of kaolin and playgorskite, which optionally further include zeolite. Where two or more layered clays are present in the hemostatic composition, the relative amounts of the layered clays can be varied to one another.

In other embodiments, the hemostatic composition can include a combination of a cation-loaded layered clay (e.g., a calcium-loaded layered clay) with a layered clay that, for example, carries a different cation and/or has not been subjected to cation-exchange. In other embodiments, the hemostatic composition can include a combination of a layered clay that has been modified to carry a agent of interest (e.g., an antibiotic, clotting factor, thrombin, etc.) with a layered clay that has not been so modified (e.g., a natural clay).

As will be discussed below, hemostatic compositions composed of a combination of a wet layered clay (e.g., wet kaolin, smectite, montmorillonite, saponite, palygorskite, and/or sepiolite) and an at least partially dehydrated zeolite, including hemostatic compositions having a wet layered clay:zeolite present in the hemostatic compositions at a amounts disclosed herein, are of particular interest. For example, exemplary wet kaolin:zeolite ratios (weight:weight), where the zeolite is at least partially dehydrated (including dry zeolite), include all ratio ranges exemplified above, including ratio ranges from at least 1:1 to 7:5, 1.5:1 to 7:4, 1.5:1 to 7:3, 1.5:1 to 7:2, 1.5:1 to 7:1, 1.5:1 to 6:5, 1.5:1 to 6:1, 1.5:1 to 5:3, 1.5:1 to 5:2, 1.5:1 to 5:1, 1.5:1 to 4:3, 1.5:1 to 4:1, 1.5:1 to 3:2, 1.5:1 to 3:1, 1.5:1 to 7:2, to 2:1, and the like, including 2:3, 1:3, 1.5:1, 2:1, 3:1, 3:2, 4:1, 4:3, 5:1, 5:2, 5:3, 6:1, 6:5, 7:1, 7:2, 7:3, 7:4, 7:5 and the like. Ratios of wet layered clay to at least partially dehydrated zeolite of greater than 1:1, 1.5:1 or greater, 2:1 or greater, 2.5:1 or greater, 3:1 or greater, 3.5:1 or greater, 4:1 or greater, 4:3 or greater, 5:1 or greater, 5.5:1 or greater, 6:1 or greater, 6.5:1 or greater, 7:1 or greater, 7.5:1 or greater are also contemplated herein. Further exemplary hemostatic compositions having a wet layered clay (e.g., wet kaolin) and an at least partially dehydrated zeolite contemplated herein include those in which the layered clay is present at greater than 50 wt %, 55 wt % or great, 60 wt % or greater, 65 wt % or greater, 70 wt % or greater, 75 wt % or greater, 80 wt % or greater, 95 wt % or greater, and up to 100 wt %, where wt % in this context indicates the weight of layered clay expressed as a percent of total combined weight of layered clay and at least partially dehydrated zeolite.

In another embodiment, the hemostatic composition includes hemostatic agents that differ in hydration state. For example, a first hemostatic agent can be hydrated (e.g., kaolin or other layered clay described herein) and a second hemostatic agent (e.g., zeolite) can be at least partially dehydrated, including fully dehydrated zeolite. It should be noted that where the hemostatic compositions is a provided as a mixture of a wet layered clay and an at least partially dehydrated zeolite, it is possible that at least some of the physically bound water of the wet layered clay (e.g., wet smectite or kaolinite) may be transferred to the zeolite during storage. However, where the surface water present on the layered clay is relatively small (e.g., as in kaolin), even if this water is completely transferred to the dry zeolite this would likely not be sufficient water to attenuate the heat release by the zeolite upon contact with blood, nor enough to significantly change the clotting properties of zeolite, and thus should not significantly affect the hemostatic activity of the hemostatic composition. Where the layered clay may naturally contain sufficient surface water (e.g., physisorbed water) such that transfer to at least partially dehydrated zeolite may occur, the layered clay can be at least partially dehydrated prior to combining with the at least partially dehydrated zeolite and/or can be maintained as separate from the at least partially dehydrated zeolite until time of use or not subjected to storage with the at least partially dehydrated zeolite for a period of time that would adversely affect the hemostatic activity of the hemostatic composition (e.g., such hemostatic compositions could be indicated as having a shorter shelf life for optimal hemostatic activity).

In one embodiment, the ratio of layered clay hemostatic agent to zeolite (e.g., at least partially dehydrated zeolite) in the hemostatic compositions is selected so as to provide a desired temperature of the hemostatic compositions upon contact with water (e.g., as is present in blood). In general, a desired local temperature for the hemostatic composition local upon contact with water is a temperature that reduces risk of burning the subject, with a temperature less than that exhibited by bound zeolite (e.g., QUIKCLOT®) or unbound zeolite (e.g., zeolite 5A powder) being generally desirable, which temperatures are in the range of 90° C. as measured by thermal imaging as described herein. Exemplary local temperature ranges for hemostatic compositions having different ratios of layered clay:zeolite (e.g., kaolin:zeolite) include target temperature ranges of 15° C. to 85 C., 25° C. to 80° C., 35° C. to 75° C., 40° C. to 70° C., and 50° C. to 60° C. In general, it is desired that the hemostatic compositions not raise the temperature at the site of the wound to a temperature that is associated with severe burns, e.g., not greater than 50° C.

In another, related, embodiment, the ratio of hemostatic agents is selected to provide for a desired clotting parameter of hemostatic activity, e.g., a desired clotting time (as measured from time of contact with blood), clotting rate, and/or clot strength. Exemplary clotting times include those that are less than 5 minutes, less than 4.5 minutes, less than 4 minutes, less than 3.5 minutes, less than 3 minutes, less than 2.5 minutes, and less than 2 minutes, less than 1.8 minutes, and less than 1.5 minutes, less than 1.0 minutes as measured in vitro by TEG analysis as described herein.

Exemplary clotting rates include greater than 55 degrees, greater than 65 degrees, greater than 70 degrees, greater than 70 degrees, or greater than 75 degrees as measured by TEG analysis as described herein.

Exemplary clot strengths include 45 mm to 100 mm, 55 mm to 90 mm, usually at least 60 mm or greater as measured by TEG analysis as described herein.

Composites of Hemostatic Compositions

In one embodiment, a hemostatic composition is provided as a composite such that the active surface area of the layered clay (e.g., kaolin) is maintained and the heat of hydration of zeolite is reduced. This can be accomplished by, for example, forming a composite of kaolin and a zeolite (e.g., zeolite 5A), and coating the composite onto the surface of large diameter (in the range of 1 mm) and large pore (greater than 50 nm) silicate materials. The large pores can provide access for the plasma proteins to the layered clay (e.g., kaolin) surfaces and provide for distribution of heat generated by the zeolite. Use of larger particles will also enable delivery of the hemostatic composition with little dust generation, and will facilitate removal from wounds.

Composites of hemostatic compositions can be made by coating silica sand (e.g., particles between 0.25 and 0.5 mm diameter) with a layered clay (e.g., kaolinite, illite, and smectite) that retains the wettability and surface charge of the clay. Exemplary methods for coating silica is described in Jerez et al. "Coating of silica sand with aluminosilicate clay." Journal of Colloid and Interface Science 2006, 294, (1), 155-164. One exemplary procedure involves physically mixing an aqueous slurry of a layered clay, zeolite, polyvinyl alcohol (200 kg/mol), and sand (silica particles), and then drying the mixture at 80° C. The dried silica particles are then washed with water, and dried again at 80° C. The clay coated silicates can exhibit enhanced surface areas compared to the silicates alone, with a coating stable under at least physiological pH, and may be stable from pH 3-11.

Such multi-component systems can also be synthesized through in-situ crystallization of zeolites on a substrate (see, e.g., Liu et al. Microporous and Mesoporous Materials 2003, 66, 117), or by chemically linking zeolites to various substrates (see, e.g., Ha et al. Advanced Materials 2000, 12, 1114; Yoon, Accounts of Chemical Research 2007, 40, 29). For example, the method of Liu et al. can be adapted to initiate the crystallization of the zeolite on the surface of kaolin or other layered clay. This method can also be adapted to initiate the crystallization of zeolites on the surface of other inorganic materials, such as porous and nonporous silicates.

In another method, zeolites can be linked to the surface of an inorganic substrate, such as a clay or silicate material, via attachment of a chemical linking group (such as 3-halopropylsilyl reagents) to the surface of either the zeolite crystal or the substrate and the subsequent reaction of the linking group with the hydroxylated surface of the zeolite or substrate (see Ha et al. and Yoon, supra). The linking group can be varied to result in covalent, ionic, and hydrogen bonding between the zeolite and the substrate, as well as physical adsorption of the zeolite to the substrate. It is also possible to substitute an array of inorganic and organic substrates, resulting in a variety of composite materials including zeolite/clay composites, zeolite/silicate composites, and zeolite/textile (natural and synthetic fibers) composites.

In another method, porous and nonporous zeolite microspheres can be self-assembled by sonicating zeolite nanocrystals in a solvent with varying amounts of water and surfactant present (see, e.g., Yoon, supra).

Such composite materials can be made as multi-component systems, ranging from two-components (e.g., zeolite and layered clay) to various mixtures of different zeolites (e.g., different cation-exchanged zeolites, zeolites of different structure (e.g., 5A, Y, etc.)) and layered clays.

Additional Components

The hemostatic compositions disclosed herein can optionally include other components, which may be active or inert with respect to the activity of an hemostatic agent in the hemostatic composition in promoting clotting.

The hemostatic compositions may further include fillers (e.g., aluminum sulfate) or thickening agents that facilitate the selective application of the hemostatic composition in various forms (e.g., as a paste, gel, powder, or erodable (e.g., biodegradable) solid member).

In some embodiments, the hemostatic composition comprises an antibiotic. For example, silver ions (e.g., which may be present as a component of the hemostatic agent) can provide for antibiotic activity of the hemostatic compositions. Other antibiotics include those that retain significant antibiotic activity when subjected to the heat of hydration of the hemostatic composition. Other exemplary components can include cytokines, growth factors, and the like which can promote wound healing and/or reduce the risk of infection.

In some embodiments, the hemostatic composition includes a clot-promoting factor in addition to the clay-based hemostatic agent described herein (e.g., in addition to kaolin and/or zeolite). For example, the hemostatic compositions can a clotting factor or platelet activating agent. Exemplary agents include Factor VII, thrombin, serotonin, collagen, thromboxane A2, and/or ADP. Such components can be from a recombinant source of the same or different animal origin as the subject to be treated (e.g., human, bovine, etc.). Such agents can be incorporated into the hemostatic composition by, for example, coating the surface of the layered clay with the agent. One exemplary method is set out in the Examples below. Such hemostatic compositions find use in treatment of bleeding wounds in, for example, subjects who have a clotting factor deficiency, e.g., hemophiliacs.

In some embodiments, the hemostatic composition does not contain "tissue factor" (TF) is a cell membrane-bound glycoprotein present on subendothelial cells which is thought to function after blood vessel injury to bind Factor VIIa in blood, activating the extrinsic blood coagulation pathway to activate the common pathway for blood coagulation. (Weiss et al. 1989 Blood 73:968-75).

Modification of Oxide Surface

In some embodiments, the surface of one or more hemostatic agents in the hemostatic compositions is modified by attachment of a biologically active agent, which may be a protein, an ion, or the like. For example, the hemostatic agent surface may be modified to provide for attachment of a clotting factor (e.g., recombinant Factor VII), silver ions, heat shock protein (HSP), and the like. In another example, the oxide surface of a hemostatic agent can be functionalized with, e.g., organosilanes, amino acids, carboxylic acids, and/or phosphate groups, to promote the attachment of clot promoting reactants, antibiotics, and/or other elements that can provide a desired therapeutic effect at a wound.

Dosage Forms and Carriers

The hemostatic compositions of the disclosure can be provided in a variety of dosage forms, and, optionally, can be provided in combination with a variety of different, compatible carriers. Exemplary carriers include those which facilitate application to a wound, e.g., by facilitating delivery of the hemostatic composition from its packaging and to a wound, facilitating application and/or maintenance at a wound site, and the like. Accordingly, the hemostatic compositions, where compatible with the hemostatic activity of the hemostatic composition, can be provided as a dry formulation (e.g., a powder or other formulation that does not contain a liquid as a carrier), a paste, gel, or the like. In one embodiment, the hemostatic composition is provided as a dry, flowable dosage form that can be dispensed from a container (e.g., from a pouch or other sealed container).

It should be understood that a "hydrated" or "wet" compound can be provided in a composition without an aqueous carrier, e.g., without added water. The terms "hydrated" or "wet" in the context of a "hydrated compound" or "wet compound" refers to the state of hydration of the compound, and does not require the presence of water exogenous to the compound, i.e., water that is not physisorbed water or chemisorbed water. Thus a "hydrated hemostatic agent" (e.g., a "hydrated" or "wet" layered clay, e.g., "hydrated kaolin" or "wet kaolin") can be provided in, for example, a hemostatic composition that that does not contain exogenous water as a carrier.

Methods of Making Hemostatic Compositions

The present disclosure also provides methods of making hemostatic compositions as described herein. In general, the methods involve combining a layered clay (usually in hydrated form), and a zeolite to provide a mixture of layered clay and zeolite. Where the zeolite is at least partially dehydrated, the moisture content of the zeolite is adjusted to a desired specific moisture content (e.g., as described above) and then combined with the layered clay to form the hemostatic compositions. The mixture can then be stored in a suitable container, e.g., in a water vapor-resistant container, optionally under an air-tight and/or vacuum seal.

In one exemplary method, a hemostatic composition is produced by mixing wet kaolin with an at least partially dehydrated zeolite to form a mixture (e.g., a homogenous mixture) of the kaolin and the zeolite. The disclosure further contemplates hemostatic compositions made by such methods.

Hemostatic Devices

The hemostatic compositions disclosed herein can be provided in connection with a device adapted for storage and/or delivery of a hemostatic composition to a bleeding wound. As discussed above, the hemostatic composition is generally provided in a sterile container, which may further provide a water vapor resistant barrier to prevent rehydration of material contained therein. This latter feature may be of particular interest where the hemostatic compositions contains a partially dehydrated hemostatic agent (e.g., zeolite). Where rehydration of the hemostatic compositions is to be avoided, the hemostatic compositions can be packaged in the container under a vacuum and the container provide an air-tight seal.

The container can be in the form of a pouch (e.g., a mylar pouch), canister, tube, or other container. It is of interest to provide the container with a frangible portion to facilitate rapid opening of the container to provide for quick access to and delivery of the hemostatic composition contained therein.

The hemostatic compositions can be provided in conjunction with a variety of different devices, which can be adapted to facilitate application of the hemostatic composition to a bleeding wound. For example, the hemostatic composition can be packaged in the same or separate container with one or more of a sterile sponge, gauze, bandage, swab, compression bandage, pillow (e.g., to facilitate application to a head wound), sleeve (e.g., for covering a wound on a limb), and the like. In one embodiment, the device serves as a substrate for the hemostatic composition, where one or more of the hemostatic agents in the hemostatic composition can be adhered to the device. For example, the hemostatic composition can be provided on at least a surface of a blood-accessible surface of the device (e.g., as a surface coating), and/or within the device (e.g., permeating at least a portion of an absorbent material, such as gauze). It is to be understood that a "coating" is at least on the surface of the substrate to which it is applied, and may permeate beyond the surface, particularly where the substrate is an absorbent material.

Where the hemostatic compositions contains more than one hemostatic agent, the hemostatic agents may be present as a loose mixture (e.g., as in a pouch to be opened prior to use).

In another embodiment, one or more of the hemostatic agents of the hemostatic composition is provided as a coating on a substrate. For example, a mixture of two hemostatic agents (e.g., kaolin and zeolite) may be provided as a coating on a substrate. Alternatively or in addition, a first hemostatic agent (e.g., zeolite) may be provided as a coating on a substrate (e.g., bandage or sponge) and the second hemostatic agent (e.g., kaolin) provided loose and in the same sealed packaging as the substrate.

In another embodiment, the hemostatic agents are provided in a single container, but as separate components until time of use (e.g., in the same pouch, but in separate compartments). For example, where the hemostatic compositions contains two hemostatic agents, each hemostatic agent may be provided in two separate compartments of a container (e.g., pouch) so that the two hemostatic agents are not mixed until the container is opened just prior to use. In other embodiments, the container has a plurality of separate compartments (e.g., 2, 3, 4, 5, 6, 7, 8, 10, etc.) which are adapted to contain a desired amount of each hemostatic agent, and the hemostatic agents are divided among the plurality of compartments to provide a desired ratio of the hemostatic agents in the final hemostatic compositions. Prior to use, the hemostatic agents in the different compartments are allowed to mix, either at the site of the wound or prior to reaching the site of the wound. Mixing of the components can be facilitated by agitation during delivery through a common exit.

Figure 4:
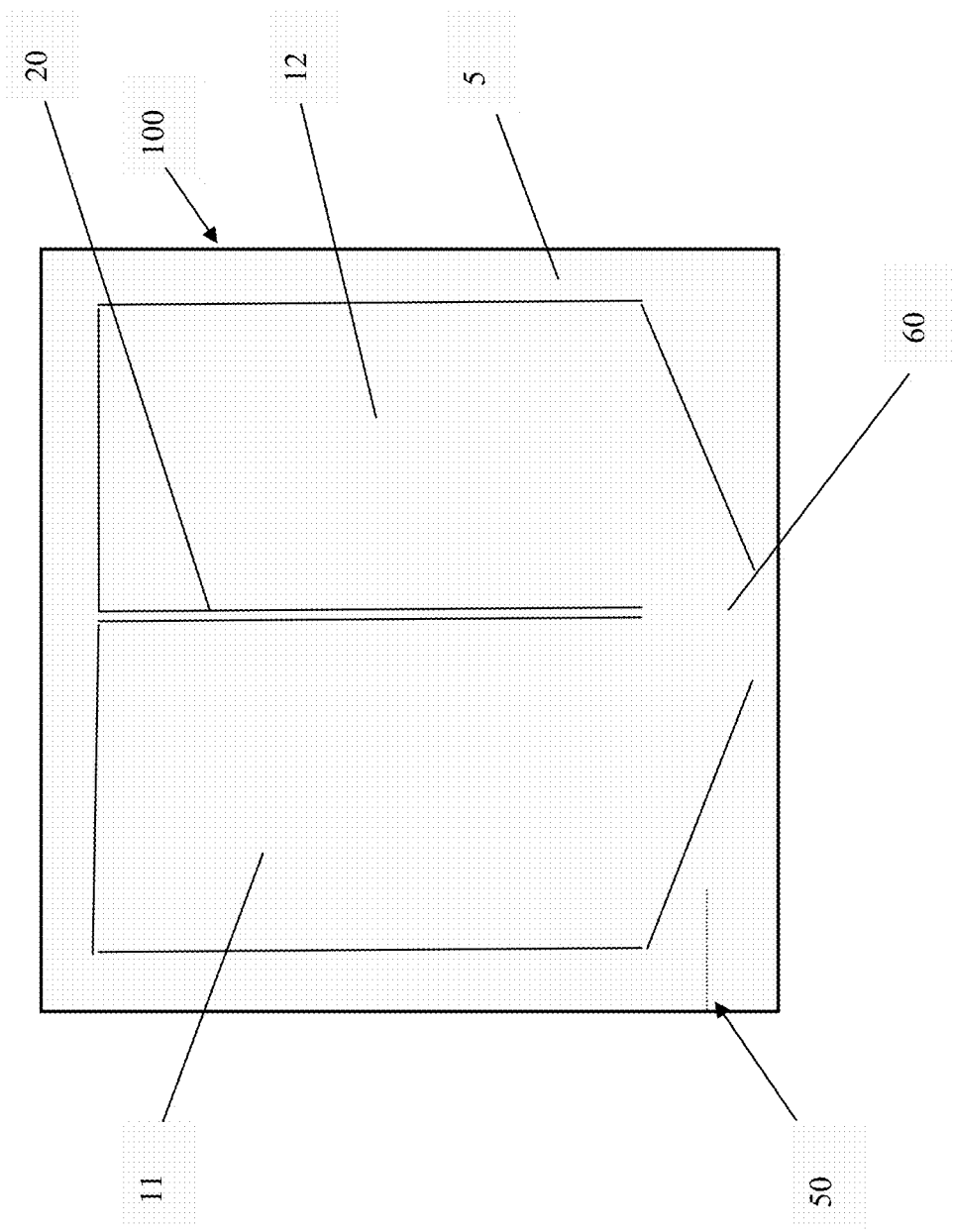
FIG. 4 is a schematic of an exemplary device for maintaining hemostatic agents of a hemostatic composition as substantially separate until use.

For example, as illustrated in FIG. 4, the device can be a sealed pouch 100 composed of a water-vapor resistant material 5 that defines at least two compartments, exemplified as 11 and 12, FIG. 4. Exemplary compartments 11 and 12 are at least partially separated by a wall(s) 20 such that at least a portion, usually most, of hemostatic agents contained in compartments 11 and 12 are not in physical contact, due to the presence of wall(s) 20. Compartments 11 and 12 terminate in a funnel-shaped outlet 60 defined by pouch material 5. When used, the pouch is opened along frangible portion 50, to that the opening necessitates opening across outlet 60. As hemostatic agents in compartments 11 and 12 pour out of the device, the hemostatic agents are mixed at outlet 60 to provide for mixed components at the wound.

In another embodiment, wall(s) 20 can be frangible. In this embodiment, the hemostatic agents in compartments 11 and 12 can be mixed prior to opening the pouch by twisting the pouch or crushing the pouch at an outer surface so as to break wall(s) 20. The hemostatic agents in compartments 11 and 12 can then be mixed inside the pouch (e.g., by agitating the pouch, e.g., by shaking), and the hemostatic composition dispensed by opening the pouch along frangible portion 50 to open a delivery outlet through which the hemostatic composition can be dispensed. In this latter embodiment, compartments 11 and 12 may optionally terminate in a funnel-shaped outlet 60, or frangible portion 50 may provide for an opening sufficient to provide for delivery of the mixed hemostatic agents.

Methods of Use of Hemostatic Compositions and Devices

The hemostatic compositions disclosed herein can be used to facilitate clotting of any external bleeding wound. As such, the hemostatic compositions can be used to enhance blood clotting in hemorrhaging blood of a subject and at least temporarily stabilize a patient that might otherwise have died as a result of exsanguination. Such methods generally involve contacting a hemostatic composition disclosed herein to a wound of a subject for a time sufficient to promote blood clot formation. The hemostatic composition can be contacted with the wound by, for example, pouring the hemostatic composition into the wound. Alternatively or in addition, the hemostatic composition can be delivered by applying a hemostatic device to the wound, where the device has an hemostatic composition coated on a substrate. Contact can be maintained through application of pressure, and may be held in place either by hand and/or through use of a bandage.

Contact is maintained at least until blood flow from the wound has slowed or has detectably ceased, i.e., until the wound is stabilized through formation of a clot. Once the clot is formed, the hemostatic composition can be removed from the wound. Where necessary, the wound can be irrigated to remove any loose hemostatic agent in the wound.

These methods are applicable to a variety of different types of wounds, which may have been inflicted intentionally or through accident and at any portion of the body amenable to application of a hemostatic composition disclosed herein. The hemostatic compositions find use in wounds of all degrees of severity ranging from bleeding skin surface wounds to wounds involving laceration of the femoral artery or other major artery or vein.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is average molecular weight, temperature is in degrees Celsius, and pressure is at or near atmospheric.

Materials and Methods

The following materials and methods were used in the Examples below.

Materials and Methods

Water Content of Kaolin and Thermogravimetric Analysis (TGA).

The water content of Kaolin was measured on a Mettler Toledo TGA/sDTA 851e. During the analysis, the mass of the sample is monitored by a highly sensitive balance as the sample is heated. The instrument records the loss of sample mass upon heating, which is due either to water loss or to a change in sample composition. The mass of kaolin was monitored in the temperature range 25° C. to 800° C. The data shows a mass loss of 0.5 to 0.6% between 25° C. and 200° C., and a mass loss of 14% at 500° C. The mass loss at 500° C. is most likely due to a change in the structure of kaolin, while the loss at 200° C. is due to the removal of any physically bound surface water. Therefore, the water content of "wet" kaolin (i.e., kaolin under ambient conditions) as measured by thermogravimetric analysis is less than 1% w/w, with a water content ranging from 0.5% or 0.6% up to 1%. "Wet kaolin" as used in these Examples refers to kaolin as it is received from the manufacturer Sigma Aldrich, without any drying treatment, and includes kaolin that is used in or out of the dry box. It should be noted that all samples were tested using wet kaolin, dry QUIKCLOT®, or dry zeolite 5A, unless otherwise stated Thrombelastograph (TEG) Measurements.

Porcine platelet poor plasma (PPP) was prepared by centrifugation of citrate-stabilized porcine whole blood at 10,000 RPM for 30 minutes. The plasma was used within one week of being drawn. Sheep and porcine whole blood were used as received within 3 days of being drawn. A Haemoscope Thrombelastograph™ was used to asses the clotting properties of all materials investigated. This instrument provides quantitative data regarding time until clot formation (R), rate of clot formation, (Alpha) and strength of the clot formed (MA) by measuring the torsion of a small sample of blood around a wire as it clots. First, 20 µl of 0.2 M $CaCl_2$ were added to a plastic cup heated to 37.5° C. Next, 340 µl of whole blood or plasma was added to the cup, followed immediately by addition of the clotting agent. Finally, the sample cup is loaded into position for commencement of the measurement. The time between sample loading and analysis is minimized to approximately 15 seconds.

Clotting Agent Preparation.

The following methods were used in preparation of clotting agent materials.

QUIKCLOT® Alone.

The QUIKCLOT® package (granular form) was opened in an argon dry box. From this package, the appropriate weight of QUIKCLOT® (20 mg±0.2 mg) was measured into glass vials with lids within the dry box, and only removed from the dry box within 30 minutes of use. After adding the $CaCl_2$ and plasma to the TEG cup as described above, the vial was opened and the contents poured into the plasma immediately prior to starting measurement. The packaged QUIKCLOT® is only opened inside the dry box, in an Argon atmosphere to preserve the dehydrated state. Dry QUIKCLOT® can also be prepared by heating the material to 200° C. or 250° C. in a vacuum oven overnight, and transferring the dried material to a dry box for storage. Hydrated QUIKCLOT is prepared by weighing 20 mg of dry QUIKCLOT into a 1 dram glass vial inside the argon atmosphere glove box. Next, the pre-weighed sample is removed from the argon atmosphere and stored under ambient conditions, uncapped for at least 24 hours prior to use in the TEG. Storing the sample at ambient conditions allows the material to adsorb water from the atmosphere and become hydrated.

Kaolin Alone.

After verifying the contents of the package by X-ray diffraction, the kaolin was used as received from the commercial supplier Sigma Aldrich (St. Louis, Mo.). Kaolin clay was weighed in ambient conditions into glass vials (20 mg±0.2 mg), and delivered to the TEG cup in the same manner as QUIKCLOT®. From thermogravimetric analysis (data not shown), the hydration levels of kaolin handled in ambient humidity are interpreted to be less than 1%. After removal from the manufacturer's bottle, (Sigma Aldrich) bottle and handled under ambient conditions is considered "wet" kaolin for these Examples.

Palygorskite (a.k.a. Attapulgite) Alone.

The material was used as received from Z-Medica corporation. Palygorskite (attapulgite) clay was weighed in ambient conditions into glass vials (20 mg±0.2 mg), and delivered to the TEG cup in the same manner as QUIKCLOT®.

QUIKCLOT®-Kaolin Mixture for Porcine Plasma and Sheep Whole Blood.

The appropriate weight of QUIKCLOT® and kaolin were measured into glass vials, in the glove box and under ambient conditions, respectively. After adding $CaCl_2$ and plasma or blood to the TEG cup as described above, the kaolin was added to the QUIKCLOT® in the vial, inverted one time, and the contents of the vial, now containing both QUIKCLOT® and kaolin added immediately to the TEG cup.

Zeolite 5A Powder.

Molecular sieve zeolite 5A powder was purchased from AirGas West (Ventura, Calif.). Upon arrival, the zeolite was rinsed once with deionized water and filtered by vacuum filtration. The filter and the zeolite powder were dried at 80° C. for 1 hour to remove the excess water. Hydrated zeolite 5A powder was prepared by storing the dried powder in an uncapped glass vial at ambient conditions for at least 24 hours prior to use. Dehydrated zeolite 5A was prepared by collecting and distributing the dried zeolite in glass vials, with a maximum bed height of 5 millimeters. Finally, the zeolite was dried in a vacuum oven at 200° C., overnight, and immediately transferred to an Argon atmosphere glove box (dry box). The appropriate weight of Zeolite 5A (20 mg+/−0.3 mg) was measured into glass vials, sealed with caps, and removed from the dry box within 30 minutes of use. In the thrombelastograph data reported herein, approximately half of the sample remained in the vial after adding the clotting agent to blood. Therefore, the sample weight reported in the measurement is 10 mg.

Y-Type Zeolites.

Y-Type zeolites (Faujasites) were purchased from Zeolyst International (Valley Forge, Pa.). Upon arrival, the zeolites were ion-exchanged from their native form to the calcium form by soaking in a solution of calcium chloride for 30 minutes. The solid material was collected by centrifugation and the ion-exchange process was repeated two times. The naming system denoted herein assigns the native form of the zeolite first (Na or H), then the manufacturers name for the zeolite (e.g., CBV 100), followed by the ion-exchanged form of the zeolite (Ca). After ion-exchange, each sample was rinsed three times with deionized water and filtered by vacuum filtration. The filter and the zeolite powder were dried at 80° C. for 1 hour to remove the excess water. The dried zeolite powder was then collected and distributed in glass vials, with a maximum bed height of 5 millimeters. Finally, the zeolite was dried in a vacuum oven at 200° C., overnight, and immediately transferred to an Argon atmosphere glove box (dry box). The appropriate weight of each zeolite (20 mg+/−0.3 mg) was measured into glass vials, sealed with caps, and removed from the dry box within 30 minutes of use.

Sodium Exchanged Zeolites.

Zeolite CBV 100, 4A, and 13X powders were purchased as the sodium form of the zeolites from AirGas West (Ventura, Calif.). Upon arrival, the zeolites were rinsed once with deionized water and filtered by vacuum filtration. The filters and the zeolite powders were dried at 80° C. for 1 hour to remove the excess water. Dehydrated zeolite powders were prepared by collecting and distributing the dried zeolites in glass vials, with a maximum bed height of 5 millimeters. Finally, the zeolites were dried in a vacuum oven at 200° C., overnight, and immediately transferred to an Argon atmosphere glove box (dry box). The appropriate weight of each zeolite sample (20 mg+/−0.3 mg) was measured into glass vials, sealed with caps, and removed from the dry box within 30 minutes of use.

Scanning Electron Microscope (SEM) Imaging.

A small amount (~100 mg) of clay was added to a 1.5 ml centrifuge tube containing deionized water and mixed to suspend the clay. In order to image the clay platelet sizes present after their immersion in aqueous media (plasma), the immersed clays were dried by lyophilization in order to minimize the aggregation caused by surface tension during evaporation. Each lyophilized clay sample was affixed to an aluminum SEM stub using conductive carbon tape, and coated with Au/Pd using an argon plasma deposition system. Images were obtained using an FEI XL30 SEM at an accelerating voltage of 5 kV Calcium Ion Concentrations in Simulated Body Fluid after Exposure to Layered Clays.

Simulated Body Fluid (SBF) was prepared according to the protocol for SBF-i in Oyane et al. (Oyane et al. (2003) "Preparation and assessment of revised simulated body fluids." Journal of Biomedical Materials Research 65A:188-195) Inductively Coupled Plasma (ICP) sample preparation: The high standard was prepared by mixing 10.0 g 18 MΩ water with 5.0 g SBF. A quality control sample was prepared by combining 10 ml 18 MΩ water with 5 ml SBF. The low standard used was 18 MΩ water. The ratio of clotting agent mass to volume of SBF was chosen to represent the mg/ml clotting agent/blood used in the TEG assays. To quantify the ions released by layered clays, 111 g of each clay was added to 2 ml SBF, inverted for 1 minute, then centrifuged for 3 minutes at 12,000 RPM. Within 7 minutes total, 1.67 ml of supernatant was removed from each centrifuge tube and added to 3.33 ml 18 MΩ water for ICP analysis. The samples were analyzed on a Thermo Jarell Ash High Resolution Iris model ICP using triplicate measurements on the same day as the sample preparation. The calcium and magnesium lines used to determine concentration were 396 nm and 285 nm, respectively.

Clay Zeta Potentials in SBF.

Simulated Body Fluid (SBF) was prepared according to the protocol for SBF-i in Oyane et al. (Oyane et al. (2003) "Preparation and assessment of revised simulated body fluids." Journal of Biomedical Materials Research 65A:188-195). Prior to analysis, clay samples (~1 mg material) were added to 3 ml SBF-i (pH 7.4) in glass vials and each sonicated for 10 minutes. The measurements were made in plastic cuvettes using a Malvern Universal Dip Cell with Pd electrodes on a Malvern Zetasizer Nano. Each measurement was made in triplicate at 25° C. using the monomodal analysis and an automatic number of runs. Between each sample, the dip cell electrode was immersed in concentrated nitric acid for 10 seconds, rinsed with deionized water, then sonicated in deionized water for 3 minutes. The zeta potential measurements for attapulgite at variable temperatures were made by adjusting the incubation temperature of the instrument to match the analysis temperature. Each sample was allowed to equilibrate at the analysis temperature for at least 5 minutes prior to analysis to ensure equal heating of the sample.

Thermal Imaging.

In vitro heat release was measured using a liquid nitrogen cooled ImagIR LC camera from Santa Barbara Focal Plane (Santa Barbara, Calif.). The thermal imaging camera was calibrated for the temperature range between 20° C. and 100° C. Experiments were filmed at a 71 Hz frame rate with a Janos Technology A ISO 25 mm F/2.3 MWIR focusing lens. The heat release of the Kaolin-QUIKCLOT® and the Kaolin-Zeolite 5A mixture samples was measured by adding 2 grams of the mixture to 10 grams of water.

QUIKCLOT®-Kaolin Mixture Preparation for Thermal Imaging.

QUIKCLOT®, as received from Z-Medica, was opened under an Argon atmosphere to preserve the hydration level of the material. Kaolin, as received from Sigma Aldrich, was transferred into the Argon atmosphere glove box without heating of the sample. It should be noted that even though the sample was transferred to the dry box, it is still considered wet kaolin because it was not heated to drive off any of the physically bound water of kaolin. The appropriate weight of QUIKCLOT® and Kaolin were measured out and mixed together under an Argon atmosphere. The mixtures were sealed in glass vials and removed from the dry box no longer than 30 minutes prior to use.

Example 1

Effect on Clotting of Porcine Plasma by Mixture of Hydrated (Wet) Kaolin and Dehydrated (Dry) QUIKCLOT®

The effect of wet QUIKCLOT®, dry QUIKCLOT®, wet kaolin, and a mixture of dry QUIKCLOT® and wet kaolin upon clotting time, clotting rate, and clot strength was assessed in porcine plasma.

For this example, wet QUIKCLOT® was prepared by removing the QUIKCLOT® from the original packaging and allowing to rest at ambient conditions for at least 12 hours to two weeks. Under ambient conditions, QUIKCLOT® will draw moisture from the air until it is fully hydrated. The fully hydrated state of QUIKCLOT® should contain approximately 18 to 20% water, by weight. Alternatively, wet QUIKCLOT® is prepared by rinsing the material with deionized water, followed by heating to 50° C. to remove the excess surface water. The sample is then allowed to rest at ambient conditions for two to three days to resorb any surface water lost during heating. This latter method is a faster and more complete method of hydrating the material, but still results in a fully hydrated state of QUIKCLOT® of approximately 18 to 20% water content, by weight. As discussed above, wet kaolin refers to kaolin having a water content of 1% or less under ambient conditions, without heat treatment.

The results are shown in Table 1.

TABLE 1

Clotting characteristics of QUIKCLOT®, Kaolin, and QUIKCLOT® Kaolin mixture in porcine plasma.

| Agent (20 mg) | R (min) | Alpha (degrees) | MA(mm) |
|---|---|---|---|
| No Added Agent N = 4 | 11.9 ± 0.7 | 49.8 ± 2.1 | 38.9 ± 1.6 |
| 20 mg Wet QUIKCLOT® N = 4 | 6.1 ± 0.2 | 48.3 ± 2.7 | 41.1 ± 0.4 |
| 200 mg Dry QUIKCLOT® N = 4 | 3.1 ± 0.4 | 54.5 ± 1.3 | 47.5 ± 1.3 |
| 20 mg Wet Kaolin N = 4 | 3.9 ± 0.2 | 70.1 ± 1.4 | 41.3 ± 1.8 |
| 5 mg Wet kaolin + 15 mg Dry QUIKCLOT® N = 4 | 2.6 ± 0.1 | 63.9 ± 0.7 | 48.1 ± 0.6 |

In thrombelastograph measurements in porcine plasma, the mixture of hydrated kaolin and dehydrated QUIKCLOT® decreased clotting times (R) compared to the same mass of QUIKCLOT® alone. In addition, this combination also provides higher clotting rates (Alpha) than QUIKCLOT® alone and higher clot strengths (MA) than kaolin alone.

Example 2

Effect on Clotting of Porcine Blood by Mixture of Hydrated (Wet) Kaolin and Dehydrated (Dry) QUIKCLOT®

In order to assess the differences between bound zeolite (i.e., without a binder) and unbound zeolite (i.e., no binder), the effect of QUIKCLOT® and zeolite 5A upon clotting of porcine whole blood was assessed. The results are shown in Table 2A.

TABLE 2A

Clotting properties of zeolite 5A powder as compared to granular QUIKCLOT® in porcine whole blood.

| Sample | R (minutes) | Alpha (degrees) | MA (mm Displacement) |
|---|---|---|---|
| Porcine Whole Blood (no agent) | 4.8 +/− 0.2 | 77.6 +/− 2.0 | 75.3 +/− 0.8 |
| 20 mg Dry QUIKCLOT® | 2.2 +/− 0.3 | 71.7 +/− 0.5 | 70.1 +/− 1.4 |
| 10 mg Dry Zeolite 5A | 2.3 +/− 0.1 | 80.4 +/− 0.5 | 71.9 +/− 2.1 |

Thrombelastograph measurements of zeolite 5A powder in porcine whole blood show that the zeolite alone induces clot formation as effectively as QUIKCLOT®. It should be noted that the clotting rate (alpha) for the zeolite 5A powder is faster than that of QUIKCLOT®. This may be due to the smaller particle size of the zeolite powder than the granular composite material. From the above, it is reasonable to conclude from the data above that a mixture of zeolite 5A (without a binder) and kaolin would perform similarly to mixtures of QUIKCLOT® (which contains zeolite with a binder) and kaolin.

In order to assess the influence of the two components of QUIKCLOT® (i.e. zeolite and clay binder) influence clotting times, the effects of QUIKCLOT®, Zeolite 5A, and Palygorskite (Attapulgite) clay were assessed relative to the clotting properties of Kaolin clay in porcine whole blood. The results are shown in Table 2B.

TABLE 2B

Clotting properties of QUIKCLOT ®, Palygorskite (Attapulgite) clay, and Zeolite 5A as compared to Kaolin Clay in porcine whole blood.

| Sample | Clotting Time (Minutes) | |
|---|---|---|
| Porcine Whole Blood | 4.6 | 0.1 |
| 20 mg Dehydrated QUIKCLOT | 2.1 | 0.2 |
| 20 mg Dehydrated Zeolite 5A | 2.5 | 0.4 |
| 20 mg Hydrated QUIKCLOT | 4.3 | 0.1 |
| 20 mg Hydrated Zeolite 5A | 2.8 | 0.1 |
| 20 mg Hydrated Palygorskite | 2.0 | 0.3 |
| 20 mg Hydrated Kaolin | 2.2 | 0.2 |

Thrombelastograph measurements in porcine whole blood (Table 2B) show that Palygorskite clay, which is present in QUIKCLOT® as a binding agent, has a clotting time that is comparable to the clotting time of Kaolin clay, dehydrated QUIKCLOT®, and dehydrated Zeolite 5A. It should also be noted that both hydrated zeolite 5A and hydrated Palygorskite clay have faster clotting times in porcine whole blood than hydrated QUIKCLOT®. The faster clotting times of hydrated Zeolite 5A and hydrated Palygorskite relative to hydrated QUIKCLOT® may be influenced by the smaller particle sizes of the Zeolite 5A and Palygorskite materials relative to the particle size of granular QUIKCLOT®. It is reasonable to conclude from these results that a mixture of the Zeolite 5A powder with either Kaolin or Palygorskite clays would perform similarly to mixtures of QUIKCLOT® and Kaolin, and that both the Palygorskite and Kaolin clays would perform as effective hemostatic agents without zeolite.

Example 3

Effect on Clotting of Whole Sheep Blood by Mixture of Wet Kaolin and Dry QUIKCLOT®

The clotting properties of dry QUIKCLOT® and wet Kaolin in whole sheep blood are shown in Table 3 below. These data are also represented in FIG. 1.

TABLE 3

Clotting properties of the QUIKCLOT ®/Kaolin mixture in sheep whole blood.

| Sample | R (minutes) | Alpha (degrees) | MA (mm Displacement) |
|---|---|---|---|
| Sheep Whole Blood (no agent) | 10.7 +/− 0.1 | 40.9 +/− 1.7 | 66.1 +/− 1.5 |
| Dry QUIKCLOT ® (QC) | 2.7 +/− 0.2 | 58.3 +/− 2.9 | 65.7 +/− 0.5 |
| Wet Kaolin | 3.0 +/− 0.1 | 60.7 +/− 4.7 | 64.7 +/− 0.9 |
| 14 mg Dry QUIKCLOT ® + 6 mg Wet Kaolin | 2.4 +/− 0.3 | 69.7 +/− 2.6 | 60.6 +/− 1.5 |

While QUIKCLOT® and wet Kaolin have similar clotting properties alone, the combination of both materials decreases the clotting time (R). This may be due to the increased "protein-accessible" surface area presented by the addition of the layered clay kaolin.

Example 4

Effect of Zeolite Structure Upon Clotting Activity

The framework structure of a zeolite can be modified by decreasing the silicon to aluminum ratio of the zeolite. The effect of these changes in structure upon the clotting effect of zeolite was tested.

TABLE 4A

Clotting properties of Y-Type zeolites as compared to granular QUIKCLOT ® in sheep whole blood.

| Sample | Si:Al Ratio | R (Minutes) | Alpha (Degrees) | MA (mm Displacement) |
|---|---|---|---|---|
| Sheep Whole Blood | NA | 10.2 +/− 0.2 | 61.7 +/− 1.9 | 74.5 +/− 2.3 |
| QUIKCLOT ® | 1 | 2.7 +/− 0.3 | 62.2 +/− 0.8 | 72.7 +/− 0.7 |
| Na CBV 100 Ca | 2.6 | 2.3 +/− 0.0 | 74.9 +/− 3.0 | 76.5 +/− 1.7 |
| H CBV 400 Ca | 2.6 | 3.4 +/− 0.3 | 58.1 +/− 2.1 | 74.7 +/− 1.3 |
| H CBV 720 Ca | 15 | 3.2 +/− 0.1 | 58.8 +/− 0.9 | 76.6 +/− 0.6 |
| H CBV 760 Ca | 30 | 4.8 +/− 0.3 | 67.3 +/− 1.9 | 75.8 +/− 2.1 |
| H CBV 780 Ca | 40 | 3.7 +/− 0.3 | 63.8 +/− 0.3 | 76.1 +/− 1.1 |
| H CBV 901 Ca | 40 | 4.1 +/− 0.2 | 71.9 +/− 0.8 | 76.1 +/− 1.1 |

The data in Table 4A above shows that as the silicon to aluminum ratio of zeolites is increased (and thus there is less framework aluminum present), the clotting time tends to increase. Sample "Na CBV 100Ca", which is the calcium exchanged version of sodium-Y zeolite, has clotting properties similar to that of QUIKCLOT® in sheep whole blood. Therefore, sodium-Y or calcium exchanged sodium-Y zeolites may also function as an effective component of a composite material composed of a zeolite and a layered clay, such as kaolin or palygorskite.

Thrombelastograph measurements of sodium exchanged zeolites with varying Si:Al ratios were taken in porcine whole blood to investigate the influence of the ion exchange capacity of a material on the clotting response. The ion exchange capacity of a material with respect to certain cations (i.e. $Ca^{2+}$) is related to the framework structure of the material. As mentioned above, the framework structure is altered when the Si:Al ratio of the material changes.

TABLE 4B

Clotting times of sodium exchanged zeolites with varying Si:Al ratios and $Ca^{2+}$ ion exchange capacities in porcine whole blood.

| Sample | Si:Al Ratio | Clotting Time (Minutes) | |
|---|---|---|---|
| No Agent | NA | 4.4 | 0.0 |
| Na 4A | 1 | 2.9 | 0.1 |
| Na 13X | 1.2 | 2.6 | 0.2 |
| Na CBV100 | 2.5 | 2.0 | 0.3 |

The results in Table 4B show that as the Si:Al ratio increases, the clotting time in porcine whole blood decreases. Without being held to the theory, the increase in Si:Al ratio may serve to lower the ion exchange capacity of the zeolite and decrease the amount of cations (i.e. $Ca^{2+}$) that the zeolite can remove from blood. The coagulation process is known to be dependent upon the proper balance of electrolytes in blood plasma, with $Ca^{2+}$ playing a central role in forming many protein-protein bridging complexes involved in clot formation. It is reasonable to conclude from these results that the clotting times of zeolites Na 13X and Na 4A in porcine whole blood are prolonged compared to the clotting time of zeolite Na CBV 100 due to the increasing ability of zeolites Na13X and Na 4A to remove $Ca^{2+}$ from solution (Barri et al. (1980)

"Binary and Ternary Cation Exchange in Zeolites." Journal of Chromatography 201: 21-34.).

Certain layered clays, including smectites such as montmorillinite and kaolin, also have an ion exchange capacity and can remove or release cations, such as $Ca^{2+}$, in solution. The clotting times of a series of layered clays in porcine plasma were measured using a Thrombelastograph to assess the effect of ion exchange capacity on clotting properties. The results are shown below, in FIG. 5.

Figure 5:
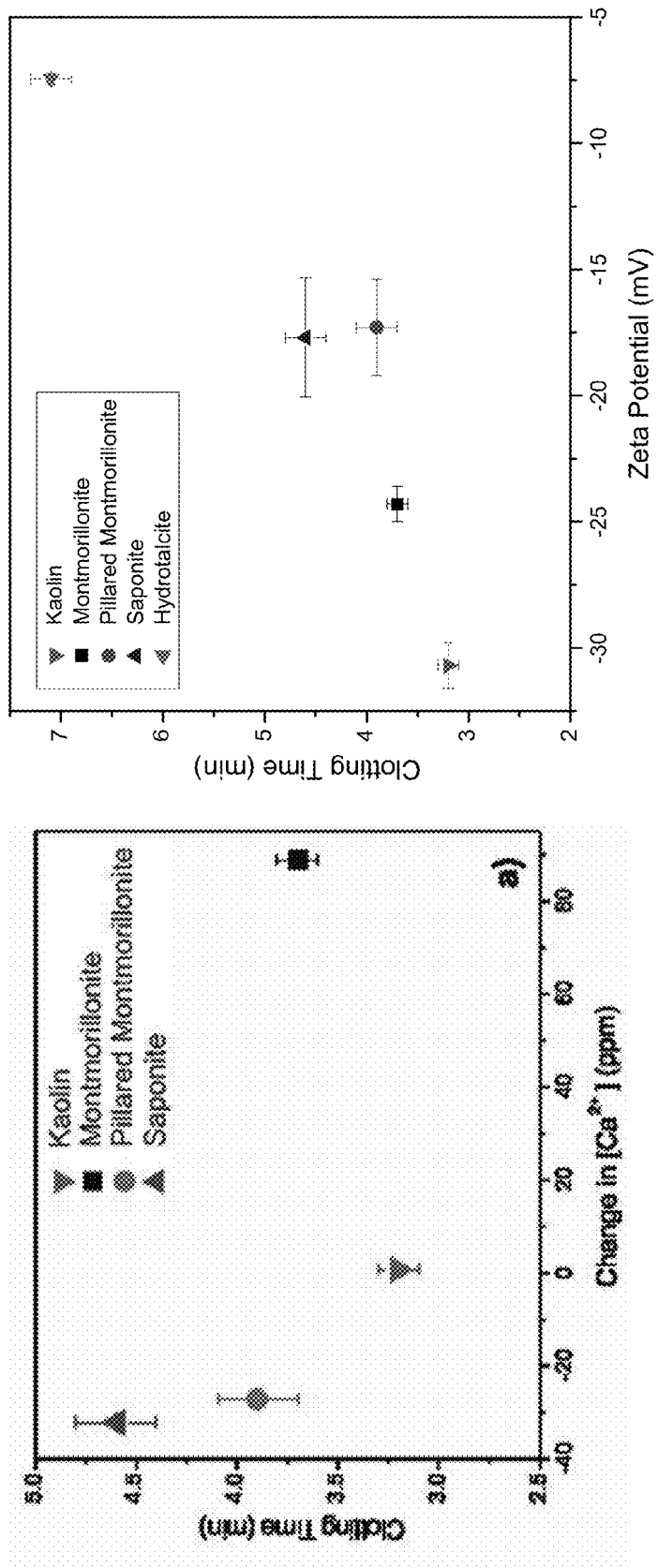
FIG. 5 is a set of graphs. The graph of the upper panel shows clotting times of layered clays in porcine plasma as a function of change in Ca2+ concentration; the graph of the lower panel shows clotting times in porcine plasma as a function of zeta potential.

The data of FIG. 5 demonstrate that layered clays which remove relatively more $Ca^{2+}$ from simulated body fluid (FIG. 5, left) have a prolonged clotting time compared to layered clays that remove relative less $Ca^{2+}$ or do not cause a detectable change in $Ca^{2+}$ concentration in the solution. This feature can be independent of surface potential. For example, Pillared Montmorillonite and Saponite have similar surface potential values in simulated body fluid (FIG. 5, right panel), but Saponite removes more $Ca^{2+}$ from the surrounding medium, making the local environment increasingly deficient in the $Ca^{2+}$ ions that facilitate clot propagation. It is reasonable to conclude from these results that the ability of a layered clay to control the local electrolyte concentration (particularly in removing $Ca^{2+}$ ions from solution) is an important metric in predicting the ability of a layered clay to act as an effective hemostatic agent.

Example 5

Heat Release of QUIKCLOT®, Zeolite 5A, and Kaolin-Containing Mixtures Thereof

Characterizing the in vitro heat release of potential hemostatic agents is important not only for assessing their potential to cause burns at the wound site, but also because an elevation in local temperature may serve to increase the clotting response. In vitro heat release was assessed for various QUIKCLOT®-Kaolin and Zeolite 5A-Kaolin mixtures when added to water. Temperature readings were taken at the hottest part of the sample.

Figure 2:
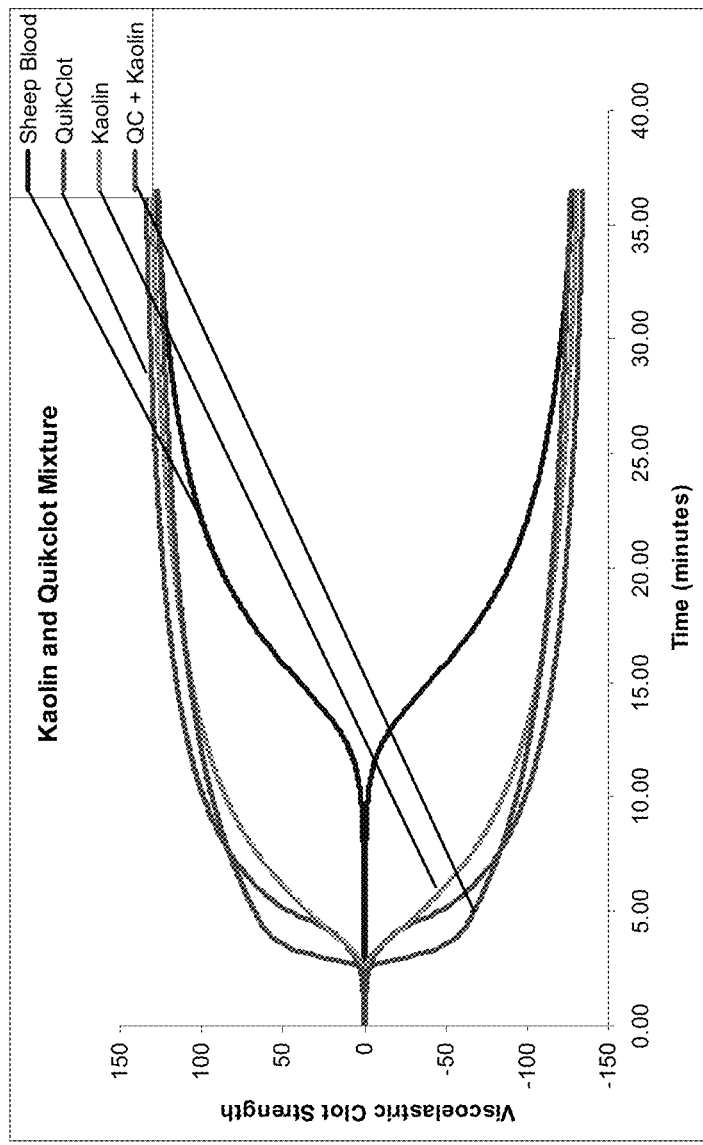
FIG. 2 is a graph showing the clotting properties of QUIKCLOT®/Kaolin mixture in sheep whole blood.

The results are shown in Table 5 below, as well as in FIG. 2. The weight percentage of dry QUIKCLOT® and dry zeolite 5A is indicated in each panel, with the remainder of the composition being wet kaolin.

TABLE 5

Local temperature changes in QUIKCLOT ®/Kaolin and Zeolite 5A/Kaolin mixtures up on the addition of water. The error associated with each measurement is +/− 5° C.

| Sample | Temperature (° C.) |
| --- | --- |
| QUIKCLOT ® | 90 |
| 75:25 QUIKCLOT ®/Kaolin | 88 |
| 50:50 QUIKCLOT ®/Kaolin | 92 |
| 25:75 QUIKCLOT ®/Kaolin | 27 |
| Zeolite 5A Powder | 88 |
| 75:25 Zeolite 5A/Kaolin | 91 |
| 50:50 Zeolite 5A/Kaolin | 77 |
| 25:75 Zeolite 5A/Kaolin | 54 |
| Kaolin | 22 |

While the heat release for the QUIKCLOT®-Kaolin mixture is not significantly attenuated until the weight % of kaolin reaches 75%, the Zeolite 5A-Kaolin mixture samples show an even heat attenuation with increase in Kaolin content. Similarly, increasing kaolin in Zeolite 5A-Kaolin mixtures also provides for heat attenuation of this unbound zeolite.

Example 6

Effect of Mixtures of Kaolin and QUIKCLOT® on Blood Clotting

The effect of different combinations of dry QUIKCLOT™ and wet kaolin upon clotting time (R), clotting rate (alpha), and clot strength (MA) was tested in porcine whole blood. The dry QuikClot and wet kaolin were prepared and delivered to the blood in the TEG cup as described above.

| Agent (20 mg) | R (min) | Alpha (degrees) | MA(mm) |
| --- | --- | --- | --- |
| No Added Agent N = 2 | 5.8 ± 0.3 | 59.5 ± 0.6 | 62.0 ± 1.1 |
| Dry QUIKCLOT ® (QC) N = 2 | 2.6 ± 0.4 | 61.6 ± 1.3 | 61.3 ± 0.2 |
| Dry Kaolin N = 3 | 2.4 ± 0.8 | 45.0 ± 5.3 | 58.9 ± 0.5 |
| Wet Kaolin N = 2 | 1.9 ± 0.0 | 66.9 ± 4.5 | 57.7 ± 5.0 |
| Dry kaolin (6 mg) + Dry QC (14 mg) N = 4 | 1.8 ± 0.5 | 55.7 ± 0.6 | 60.2 ± 2.3 |
| Dry kaolin (10 mg) + Dry QC (10 mg) N = 2 | 1.9 ± 0.4 | 55.3 ± 0.9 | 60.0 ± 0.2 |
| Dry kaolin (14 mg) + Dry QC (6 mg) N = 2 | 1.9 ± 0.1 | 55.4 ± 1.9 | 57.1 ± 1.1 |
| Wet Kaolin (10 mg) + Dry QC (10 mg) N = 2 | 1.9 ± 0.1 | 64.3 ± 4.9 | 55.8 ± 3.2 |
| Wet Kaolin (14 mg) + Dry QC (6 mg) N = 2 | 1.8 ± 0.1 | 66.6 ± 1.1 | 60.5 ± 0.7 |
| Wet Kaolin (6mg) + Dry QC (14 mg) N = 2 | 1.4 ± 0.1 | 72.5 ± 3.1 | 61.5 ± 0.6 |

The data in the table above illustrate that wet kaolin promotes clotting faster than dry kaolin. Without being held to theory, this may be due to the relative hydrophobicities of wet and dry kaolin, with wet kaolin appearing to enter blood more readily than dry kaolin, which tends to stay on the surface of the blood.

The mixture of wet kaolin and dry QUIKCLOT® at a ratio of approximately 1:2, which was mixed immediately before addition to the blood sample. Without being held to theory, the enhanced blood clotting activity of this mixture may be a result of the combined effects of the kaolin clay presenting a larger amount of material surface that is accessible to clotting factors than the QUIKCLOT® surface, while the heat generated by QUIKCLOT® provides for an accelerated clotting reaction. Thus, the combination of kaolin and QUIKCLOT® may be better than either alone as a combined result of heat generated by the QUIKCLOT® accelerating clotting reactions that occur optimally on the kaolin surface.

Figure 6:
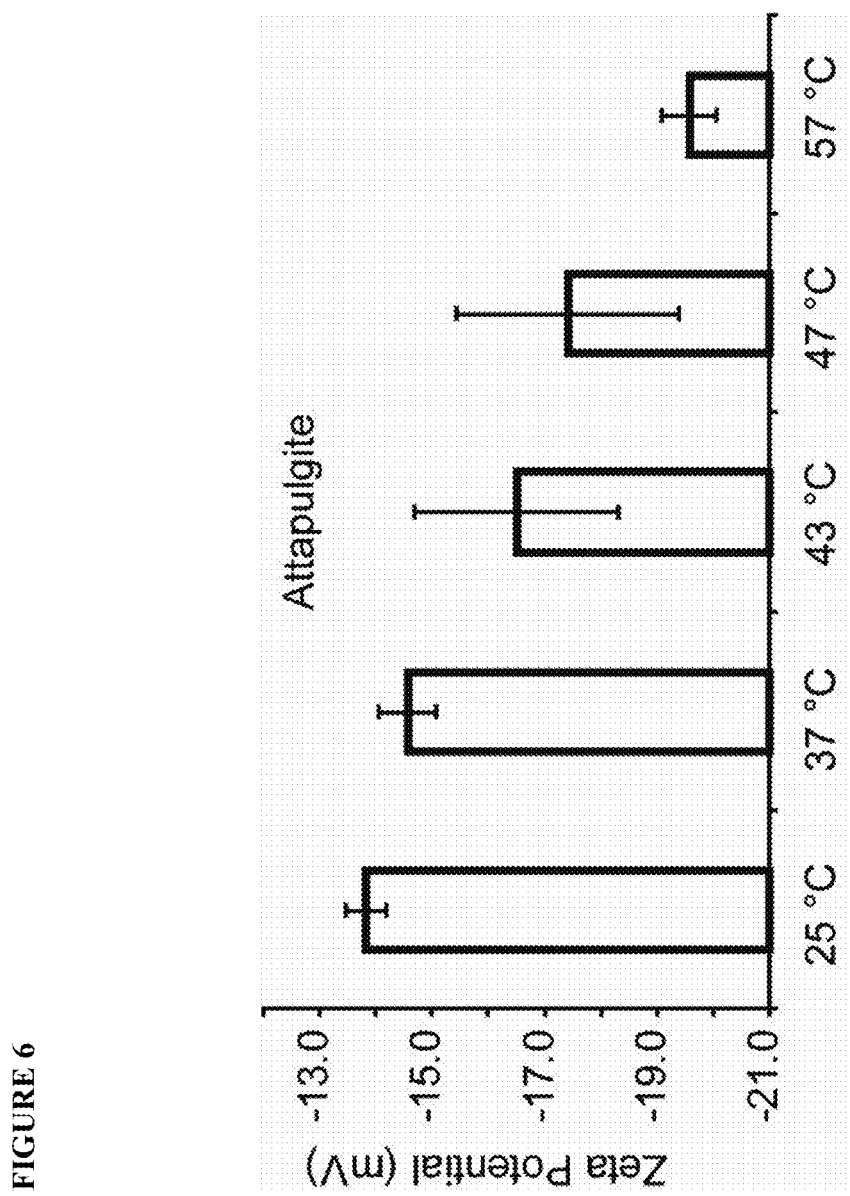
FIG. 6 is a graph showing the effect of heating on the surface potential, as measured in SBF of palygorskite (attapulgite).

The effect of heating on the surface potential, as measured in SBF, of the palygorskite (attapulgite), which is present in the form of a clay binder present in QUIKCLOT is shown in FIG. 6. These results show that the surface potential of palygorskite (attapulgite) decreases with increasing solution temperature, with the surface potential changing from −14 mV at 37° C. to −19 mV at 57° C. The thermal imaging results shown in FIG. 1 demonstrate that the in vitro heat released from QUIKCLOT® upon contact with water can reach a maximum of 90° C., which encompasses the temperature ranges studied here, and the graph in the right panel of FIG. 3 shows the clotting times of various clays decreases as the surface potential measured in SBF decreases. It is reasonable to conclude from these results that the heat released from QUIKCLOT® reduces the surface potential of the palygorskite (attapulgite) clay binder in QUIKCLOT®, making the surface of the QUIKCLOT® material a more effective surface for the activation of clotting proteins. In addition, these data indicate that the activity of palygorskite (attapulgite)

clay alone (e.g., without zeolite) as a clotting agent would be improved by the presence of heat.

Example 8

Effect of Layered Clays Upon Clotting Time and Correlation with Zeta Potential

The effect of other layered clays on clotting time of porcine whole blood was tested in vitro as described above. Specifically, the clotting activities of 15 mgs of each of wet hydrotalcite, dehydrated Pillared montmorillonite, montmorillonite, wet Pillared-montmorillonite, wet saponite, wet montmorillonite, and sodium montmorillonite was compared to the clotting activity of wet kaolin alone. The results are provided in the graph of the left panel of FIG. 3. Except for hydrotalcite, all layered clays tested provided for decreased clotting times in vitro.

The zeta potentials of layered clays was tested to determine whether there was a correlation between zeta potential and activity of the layered clay in decreasing clotting time. The zeta potential data were collected as follows. Prior to analysis, clay samples (about 1 mg material) were added to 3 ml Simulated Body Fluid (SBF) (pH 7.4) prepared according to Oyane et al. (Oyane et al. (2003) "Preparation and assessment of revised simulated body fluids." Journal of Biomedical Materials Research 65A:188-195) in glass vials and each sonicated for 10 minutes. The measurements were made in plastic cuvettes using a Malvern Universal Dip Cell with Pd electrodes using a Malvern Zetasizer Nano ZS. Each measurement was made in triplicate at 25° C. using the monomodal analysis and an automatic number of runs. Between measurement of each sample, the dip cell electrode was immersed in concentrated nitric acid for 10 seconds, rinsed with deionized water, then sonicated in deionized water for 3 minutes.

The data demonstrate that zeta potential of a layered clay immersed in SBF correlates strongly with clotting activity (FIG. 3, right panel). For example, hydrotalcite clay, which had the lowest efficacy as a clotting agent (FIG. 3, left panel), exhibited the least negative zeta potential (−7.5 mV in SBF). The zeta potential of kaolin in SBF was the most negative of the clays tested (−30.7 mV). Kaolin was the most active clotting agent of the layered clays tested. Clays measured to have intermediate zeta potentials in SBF also had intermediate clotting activities.

The trend of decreased clotting times with decreased zeta potential values in SBF holds true as long as other material properties, such as particle morphology, are held constant. The data below show that clays with similar, platelet-like morphologies have a correlation between decreased surface potential in SBF and decreased clotting times. However, when the particle morphology changes from a platelet-like shape to a needle-like shape, faster clotting times are observed with an increased surface potential as compared to the clays with the platelet-like morphology. Thus optimization of clot-promoting activity of layered clays can be independently influenced by both morphology and by zeta potential.

Figure 7:
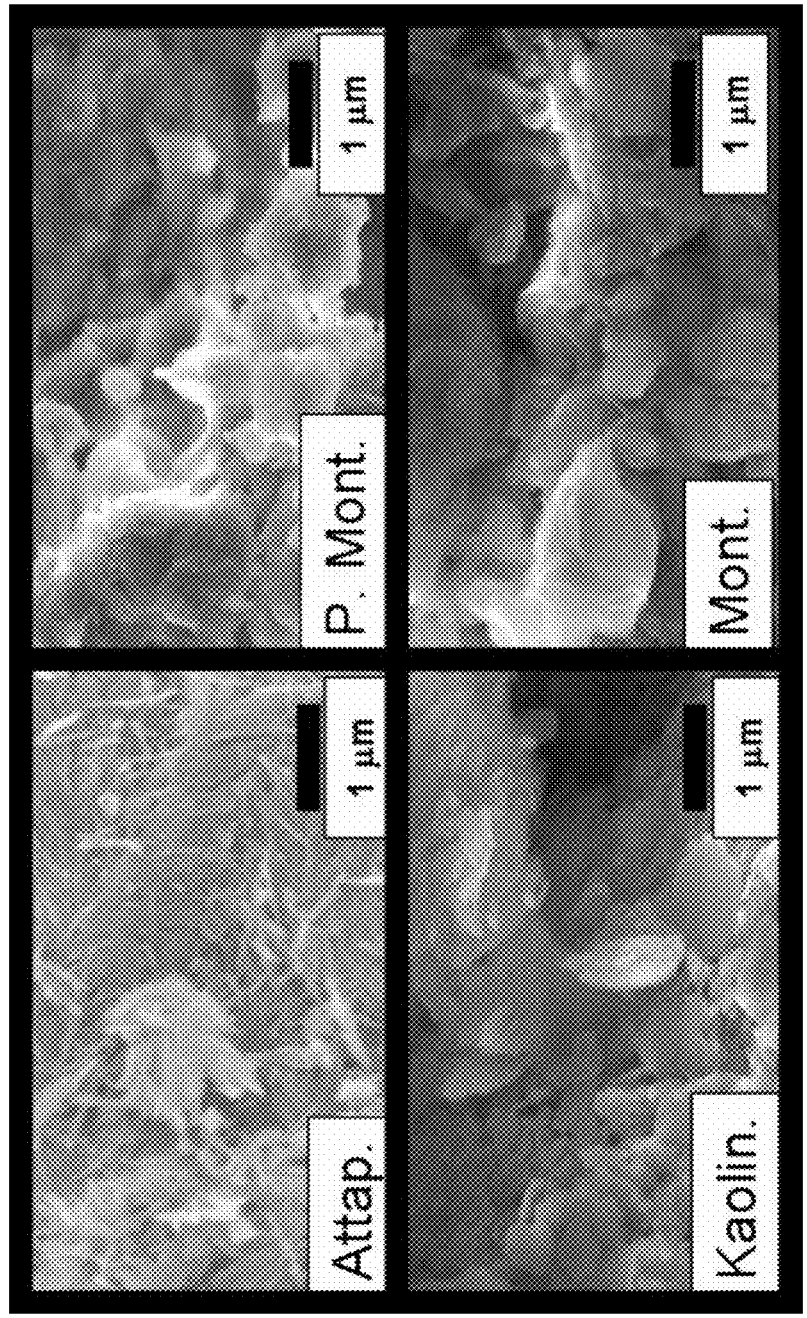
FIG. 7 are scanning electron micrographs (SEM) of palygorskite (attapulgite), pillared montmorillinite, kaolin, and montmorillinite to show the particle morphology of each clay.
Figure 8:
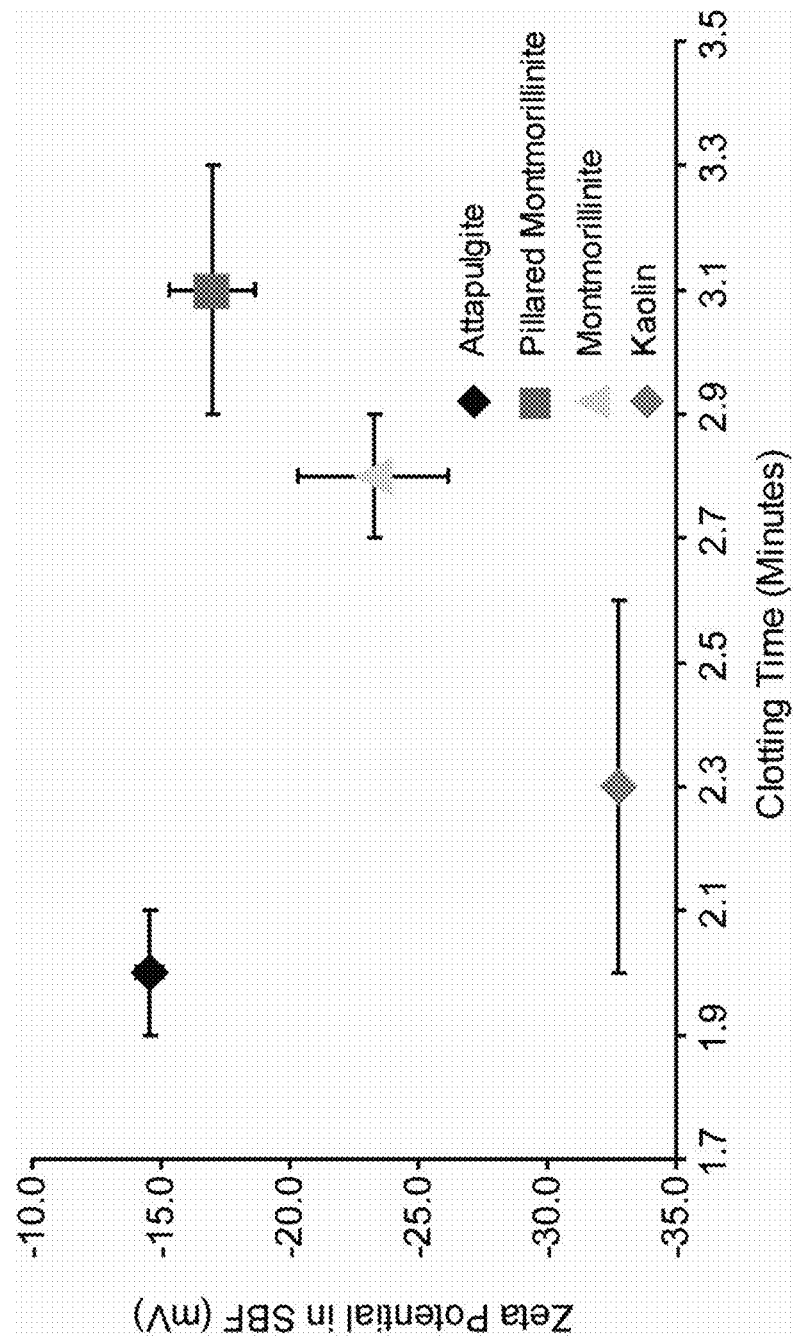
FIG. 8 is a graph showing clotting times measured with a Thrombelastograph in porcine plasma as a function of zeta potential as measured in simulated body fluid (SBF).

The scanning electron micrographs in FIG. 7. show that Pillared Montmorillinite, Montmorillinite, and Kaolin all have platelet-like morphologies with particle sizes in the range of 1-5 µm, while Palygorskite (attapulgite) clay has a needle-like morphology with sub-micrometer particle sizes. Thrombelastograph and Zeta-Potential measurements (as measured in SBF) in FIG. 9, above, show that as the surface charge decreases for the clays with platelet-like morphologies the clotting time also decreases. In contrast, the palygorskite (attapulgite) clay with the smaller, needle-like morphology has a less negative zeta potential in SBF and a faster clotting time in porcine plasma. Without being held to theory, it is likely that the smaller particles present in the palygorskite clay present a larger area of material surface that is accessible to clotting proteins and, therefore, more effectively accelerates clot initiation. It is reasonable to conclude from this data that both the zeta potential as measured in SBF and the particle morphology are influential parameters in determining the clotting response to the surface of layered clays.

Example 9

Hemostatic Compositions Containing Thrombin

As discussed above, hemostatic compositions having an additional agent that promotes clotting are contemplated by the present disclosure. Exemplary of such hemostatic compositions are those including thrombin. Thrombin, like other polypeptides, can be absorbed on the surfaces of layered clay, e.g., kaolin. An example of preparation of such a thrombin-containing hemostatic composition which uses kaolin as the exemplary layered clay is provided below.

Briefly, 800 µL of a 2 mg/ml solution of Bovine Thrombin (Sigma-Aldrich) was prepared in 20 mM HEPES buffer at pH 5.0. The absorbance of this solution at 280 nm wavelength was 0.687. At this pH, thrombin should be net positively charged, and kaolin negatively charged. After immersion of 20 mg kaolin in the thrombin solution for 24 hours at 6° C., the kaolin was removed from the thrombin solution by centrifugation and the absorbance of the solution was measured to be 0.313, indicating that roughly half of the thrombin had been absorbed on the kaolin surfaces. The kaolin-thrombin mixture was rinsed 1× with deionized water, then resuspended in about 1 ml HEPES buffer. The control kaolin sample (no thrombin) was suspended in about 1 ml HEPES buffer, and both samples were placed in 1.5 ml centrifuge tubes. The tubes were placed in a −70° C. freezer for 48 hours. The tubes were removed from the freezer and the lids were punctured with a needle, and quickly placed in a lyophilization jar, then placed under vacuum on a lyophilyzer. The tubes were lyophilized overnight, and when removed were in a powdered form, though the hydration levels of the samples were not experimentally determined.

The effect of lyophilized kaolin-thrombin and a lyophilized kaolin sample with no thrombin upon clotting was assessed using porcine whole blood as described above. Initial clotting measurements indicated that lyophilized thrombin-loaded kaolin provides for greater clot strength (MA=70.5 mm±1 mm displacement) compared to lyophilized kaolin with no absorbed thrombin (MA=60.7 mm±3.5 mm displacement).

The effectiveness of the enzyme thrombin as a clotting agent is well known, as it is used as a localized injectable in 500,000 surgical procedures annually in the U.S. Thrombin is a serine protease which effectively bypasses the entire clotting cascade, enhancing blood clot formation at the site of application regardless of clotting factor deficiencies, except in the rare cases of fibrinogen deficiencies. Additionally, thrombin also facilitates the wound healing process. Clays absorbed with thrombin or other therapeutics in this manner can be either applied as a lyophilized powder in the same manner as unmodified clay, or may be applied as a liquid suspension to an oozing wound.

Discussion of Results

The faster clotting induced by the mixture of QUIKCLOT® and Kaolin than either agent alone may be due to the fact that the addition of kaolin provides more surface area for activation of clotting factors than QUIKCLOT® alone. The QUIKCLOT® particle surface area is largely due to the presence of pores in the micropore size range, a size regime that is too small for plasma proteins to enter. In addition to providing the added surface area, the kaolin surface is a highly active clotting agent due to its negative zeta potential at the pH of blood. The data above illustrates that kaolin is a more effective clotting agent than other layered clays (e.g., montmorillonite, saponite, or hydrotalcite). The heat generated by QUIKCLOT® most likely increases the rate of clotting initiated by contact with the kaolin and QUIKCLOT® surfaces.

Palygorskite (attapulgite) clay is also an effective clotting agent as a result of the small particle size and negative zeta potential in SBF. The zeta potential of palygorskite (attapulgite) clay decreases with increasing heat, which may make the surface of the clay and QUIKCLOT more effective at clot initiation with increased heat release. The data above also show that clays and zeolites that remove $Ca^{2+}$ from solution exhibit prolonged clotting times and are less effective hemostatic agents. It can be concluded from the data above that the ability of a layered clay or other inorganic surface to effectively induce clotting is influenced by material properties such as particle size, particle morphology, surface potential as measured in SBF, in vitro heat release upon contact with blood and/or water, and the ability of the material to influence local electrolyte concentrations via ion exchange.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A device containing a hemostatic composition, the device comprising:
   a sterile container; and
   a hemostatic composition comprising a hemostatically effective amount of a wet layered clay selected from the group consisting of a kaolin, a palygorskite and a sepiolite, wherein the clay is not vitrified, and wherein the hemostatic composition is provided in the sterile container, is hydrated from 0.5 wt. % to 30 wt. %, and does not include a zeolite.

2. The device of claim 1, wherein the wet layered clay is kaolin.

3. The device of claim 1, wherein the wet layered clay is combined with a clotting factor polypeptide or a thrombin polypeptide.

4. A hemostatic composition comprising:
   a hemostatically effective amount of an isolated wet layered clay selected from the group consisting of a kaolin, a smectite, a palygorskite and a sepiolite, wherein the clay is not vitrified; and
   an isolated zeolite;
   wherein the wet layered clay and the zeolite are present in a 3:1 ratio (w/w) and provide for hemostatic activity of the composition.

5. The hemostatic composition of claim 4, wherein the zeolite is at least partially dehydrated.

6. The hemostatic composition of claim 5, wherein the zeolite has a moisture content of from 1 wt. % to 10 wt. % water.

7. The hemostatic composition of claim 5, wherein the zeolite has a moisture content of 1 wt. % to 4 wt. % water.

8. The hemostatic composition of claim 4, wherein the zeolite is disposed in a binder.

9. The hemostatic composition of claim 4, wherein the hemostatic composition is disposed on at least one surface of a device adapted for delivery of the isolated layered clay to a bleeding wound.

10. The hemostatic composition of claim 9, wherein the device is a bandage or a medical sponge.

11. A method of forming a hemostatic composition, said method comprising:
    combining a zeolite with hemostatically effective amount of a wet layered clay selected from the group consisting of a kaolin, a smectite, a palygorskite and a sepiolite, wherein the clay is not vitrified; and
    wherein said combining forms a hemostatic composition with a 3:1 ratio (w/w) of the clay to the zeolite.

12. The method of claim 11, wherein the zeolite is at least partially dehydrated prior to said combining.

13. A method of clotting blood flowing from a wound, the method comprising:
    applying the hemostatic composition of claim 1 to a bleeding wound of a subject; and
    maintaining the hemostatic composition in contact with the wound for a period of time sufficient to at least initiate blood clotting.

14. The hemostatic composition of claim 4, wherein the clay is kaolin.

15. The hemostatic composition of claim 4, wherein the clay is a smectite.

16. The hemostatic composition of claim 15, wherein the smectite is a montmorillonite.

* * * * *